United States Patent
Rudakov et al.

(10) Patent No.: US 9,017,351 B2
(45) Date of Patent: Apr. 28, 2015

(54) REDUCING FLOW THROUGH A TUBULAR STRUCTURE

(75) Inventors: Leon Rudakov, San Marcos, CA (US); Phillipe Gailloud, Towson, MD (US)

(73) Assignee: ArtVentive Medical Group, Inc., San Marcos, CA (US)

( * ) Notice: Subject to any disclaimer, the term of this patent is extended or adjusted under 35 U.S.C. 154(b) by 125 days.

(21) Appl. No.: 12/826,593

(22) Filed: Jun. 29, 2010

(65) Prior Publication Data

US 2011/0319906 A1    Dec. 29, 2011

(51) Int. Cl.
*A61B 17/08* (2006.01)
*A61B 17/12* (2006.01)
*A61B 17/00* (2006.01)
*A61B 17/22* (2006.01)

(52) U.S. Cl.
CPC ..... *A61B 17/12036* (2013.01); *A61B 17/12109* (2013.01); *A61B 17/12145* (2013.01); *A61B 17/1215* (2013.01); *A61B 2017/00469* (2013.01); *A61B 2017/1205* (2013.01); *A61B 17/12113* (2013.01); *A61B 2017/00809* (2013.01); *A61B 2017/12054* (2013.01); *A61B 2017/1209* (2013.01); *A61B 2017/22035* (2013.01); *A61B 17/1204* (2013.01); *A61B 17/12104* (2013.01)

(58) Field of Classification Search
USPC .................. 623/23.72, 1.12–1.16, 1.18–1.24, 623/1.3–1.31, 23.66, 23.7, 23.69, 623/1.24–1.26; 604/8, 192, 104; 606/194, 606/192, 198, 108, 200, 157, 158, 151, 191
See application file for complete search history.

(56) References Cited

U.S. PATENT DOCUMENTS 3,805,767 A    4/1974    Erb
3,868,956 A    3/1975    Alfidi et al.
(Continued)

FOREIGN PATENT DOCUMENTS

CN    2527227 Y    12/2002
EP    1166721 A2    1/2002
(Continued)

OTHER PUBLICATIONS

Aydogan, Transcatheter Embolization Treatment of Coronary Arteriovenous Fistulas, Asian Cardiovascular & Thoracic Annals, 2003, pp. 63-67, vol. 11, No. 1.
(Continued)

*Primary Examiner* — Jocelin Tanner
(74) *Attorney, Agent, or Firm* — James W. Hill; Nathan S. Smith; McDermott Will & Emery LLP

(57) ABSTRACT

In some embodiments, an apparatus, for reducing or stopping flow through a tubular structure of a patient, includes an elongate member arranged to form a frame having a distal and proximal opening and configured to be positioned within a lumen of the tubular structure. The frame includes a proximal, distal, and middle portion. The distal portion is tapered such that an outer cross sectional dimension (OCSD) of the distal opening is less than an OCSD of the middle portion. The frame is configured to be inverted such that the distal portion moves within and toward the middle portion for removing the frame from within the lumen. The apparatus also comprises a flow reducing member coupled to the frame such that when the frame is positioned within the lumen, the flow reducing member substantially reduces or totally obstructs flow of at least one of emboli and fluid flowing through the lumen.

12 Claims, 16 Drawing Sheets

(56) References Cited

U.S. PATENT DOCUMENTS

| | | | |
|---|---|---|---|
| 3,918,431 A | 11/1975 | Sinnreich | |
| 4,013,063 A | 3/1977 | Bucalo | |
| 4,245,623 A | 1/1981 | Erb | |
| 4,553,545 A | 11/1985 | Maass et al. | |
| 4,649,922 A | 3/1987 | Wiktor | |
| 4,682,592 A | 7/1987 | Thorsgard | |
| 4,705,517 A | 11/1987 | DiPisa, Jr. | |
| 4,706,671 A | 11/1987 | Weinrib | |
| 4,733,665 A | 3/1988 | Palmaz | |
| 4,739,762 A | 4/1988 | Palmaz | |
| 4,768,507 A | 9/1988 | Fischell et al. | |
| 4,776,337 A | 10/1988 | Palmaz | |
| 4,800,882 A | 1/1989 | Gianturco | |
| 4,827,946 A | 5/1989 | Kaali et al. | |
| 4,913,141 A | 4/1990 | Hillstead | |
| 4,969,890 A * | 11/1990 | Sugita et al. | 606/192 |
| 5,037,427 A | 8/1991 | Harada et al. | |
| 5,065,751 A | 11/1991 | Wolf | |
| 5,089,005 A | 2/1992 | Harada | |
| 5,102,417 A | 4/1992 | Palmaz | |
| 5,147,370 A | 9/1992 | McNamara et al. | |
| 5,234,437 A | 8/1993 | Sepetka | |
| 5,242,451 A | 9/1993 | Harada et al. | |
| 5,304,198 A | 4/1994 | Samson | |
| 5,324,306 A | 6/1994 | Makower et al. | |
| 5,342,387 A | 8/1994 | Summers | |
| 5,372,600 A | 12/1994 | Beyar et al. | |
| 5,417,708 A | 5/1995 | Hall et al. | |
| 5,474,089 A | 12/1995 | Waynant | |
| 5,476,505 A | 12/1995 | Limon | |
| 5,499,995 A | 3/1996 | Teirstein | |
| 5,536,274 A | 7/1996 | Neuss | |
| 5,562,641 A | 10/1996 | Flomenblit et al. | |
| 5,562,698 A | 10/1996 | Parker | |
| 5,607,445 A | 3/1997 | Summers | |
| 5,656,036 A | 8/1997 | Palmaz | |
| 5,674,287 A | 10/1997 | Slepian et al. | |
| 5,693,083 A | 12/1997 | Baker et al. | |
| 5,725,552 A | 3/1998 | Kotula et al. | |
| 5,733,329 A | 3/1998 | Wallace et al. | |
| 5,772,668 A | 6/1998 | Summers et al. | |
| 5,782,860 A | 7/1998 | Epstein et al. | |
| 5,797,952 A | 8/1998 | Klein | |
| 5,797,953 A | 8/1998 | Tekulve | |
| 5,830,222 A | 11/1998 | Makower | |
| 5,842,621 A | 12/1998 | Gschwind | |
| 5,902,266 A | 5/1999 | Leone et al. | |
| 5,922,009 A | 7/1999 | Epstein et al. | |
| 5,925,063 A | 7/1999 | Khosravi | |
| 5,925,074 A * | 7/1999 | Gingras et al. | 623/1.35 |
| 5,928,260 A | 7/1999 | Chin et al. | |
| 5,944,738 A | 8/1999 | Amplatz et al. | |
| 5,954,766 A | 9/1999 | Zadno-Azizi et al. | |
| 5,979,446 A | 11/1999 | Loy | |
| 6,010,517 A * | 1/2000 | Baccaro | 606/151 |
| 6,019,779 A * | 2/2000 | Thorud et al. | 606/198 |
| 6,024,765 A | 2/2000 | Wallace et al. | |
| 6,056,770 A | 5/2000 | Epstein et al. | |
| 6,059,825 A | 5/2000 | Hobbs et al. | |
| 6,117,157 A | 9/2000 | Tekulve | |
| 6,123,715 A | 9/2000 | Amplatz | |
| 6,168,622 B1 | 1/2001 | Mazzocchi | |
| 6,190,353 B1 | 2/2001 | Makower et al. | |
| 6,210,338 B1 | 4/2001 | Afremov et al. | |
| 6,214,042 B1 | 4/2001 | Jacobsen et al. | |
| 6,241,678 B1 | 6/2001 | Afremov et al. | |
| 6,241,758 B1 | 6/2001 | Cox | |
| 6,245,090 B1 | 6/2001 | Gilson et al. | |
| 6,248,122 B1 | 6/2001 | Klumb et al. | |
| 6,283,983 B1 | 9/2001 | Makower et al. | |
| 6,334,864 B1 | 1/2002 | Amplatz et al. | |
| 6,346,118 B1 | 2/2002 | Baker et al. | |
| 6,361,558 B1 | 3/2002 | Hieshima et al. | |
| 6,368,339 B1 | 4/2002 | Amplatz | |
| 6,371,953 B1 | 4/2002 | Beyar et al. | |
| 6,371,979 B1 | 4/2002 | Beyar et al. | |
| 6,402,760 B1 | 6/2002 | Fedida | |
| 6,402,772 B1 | 6/2002 | Amplatz et al. | |
| 6,432,116 B1 | 8/2002 | Callister et al. | |
| 6,432,127 B1 | 8/2002 | Kim et al. | |
| 6,447,531 B1 | 9/2002 | Amplatz | |
| 6,451,025 B1 | 9/2002 | Jervis | |
| 6,454,780 B1 | 9/2002 | Wallace | |
| 6,464,712 B1 | 10/2002 | Epstein et al. | |
| 6,468,301 B1 | 10/2002 | Amplatz et al. | |
| 6,506,204 B1 | 1/2003 | Mazzocchi | |
| 6,533,805 B1 | 3/2003 | Jervis | |
| 6,550,480 B2 | 4/2003 | Feldman et al. | |
| 6,554,849 B1 | 4/2003 | Jones et al. | |
| 6,562,064 B1 | 5/2003 | deBeer | |
| 6,572,643 B1 | 6/2003 | Gharibadeh | |
| 6,579,303 B2 | 6/2003 | Amplatz | |
| 6,585,760 B1 | 7/2003 | Fogarty | |
| 6,599,308 B2 | 7/2003 | Amplatz | |
| 6,602,271 B2 | 8/2003 | Adams et al. | |
| 6,616,675 B1 | 9/2003 | Evard et al. | |
| 6,623,518 B2 | 9/2003 | Thompson et al. | |
| 6,629,981 B2 | 10/2003 | Bui et al. | |
| 6,638,243 B2 | 10/2003 | Kupiecki | |
| 6,638,257 B2 | 10/2003 | Amplatz | |
| 6,638,293 B1 | 10/2003 | Makower et al. | |
| 6,645,237 B2 | 11/2003 | Klumb et al. | |
| 6,656,207 B2 | 12/2003 | Epstein et al. | |
| 6,660,020 B2 | 12/2003 | Wallace et al. | |
| 6,660,032 B2 | 12/2003 | Klumb et al. | |
| 6,663,666 B1 | 12/2003 | Quiachon et al. | |
| 6,682,546 B2 | 1/2004 | Amplatz | |
| 6,689,148 B2 | 2/2004 | Sawhney et al. | |
| 6,702,846 B2 | 3/2004 | Mikus et al. | |
| 6,719,781 B1 | 4/2004 | Kim | |
| 6,790,218 B2 | 9/2004 | Jayaraman | |
| 6,849,081 B2 | 2/2005 | Sepetka et al. | |
| 6,872,211 B2 | 3/2005 | White et al. | |
| 6,890,341 B2 | 5/2005 | Dieck et al. | |
| 6,899,730 B1 | 5/2005 | Rivelli, Jr. | |
| 6,936,058 B2 | 8/2005 | Forde et al. | |
| 6,974,473 B2 | 12/2005 | Barclay et al. | |
| 6,984,244 B2 | 1/2006 | Perez et al. | |
| 7,001,409 B2 | 2/2006 | Amplatz | |
| 7,011,671 B2 | 3/2006 | Welch | |
| 7,144,408 B2 | 12/2006 | Keegan et al. | |
| 7,152,605 B2 | 12/2006 | Khairkhahan et al. | |
| 7,220,271 B2 | 5/2007 | Sawhney et al. | |
| 7,270,668 B2 * | 9/2007 | Andreas et al. | 606/108 |
| 7,276,077 B2 | 10/2007 | Zadno-Azizi et al. | |
| 7,294,146 B2 | 11/2007 | Chew et al. | |
| 7,303,571 B2 | 12/2007 | Makower et al. | |
| 7,387,641 B2 | 6/2008 | Schmitt | |
| 7,396,362 B2 | 7/2008 | Jervis | |
| 7,398,780 B2 | 7/2008 | Callister et al. | |
| 7,458,986 B2 | 12/2008 | Schmitt | |
| 7,476,232 B2 | 1/2009 | Deal | |
| 7,582,100 B2 | 9/2009 | Johnson et al. | |
| 7,597,704 B2 | 10/2009 | Frazier et al. | |
| 7,604,649 B2 | 10/2009 | McGuckin, Jr. et al. | |
| 7,632,291 B2 | 12/2009 | Stephens et al. | |
| 7,647,930 B2 | 1/2010 | Ginn | |
| 7,651,521 B2 | 1/2010 | Ton et al. | |
| 7,666,204 B2 | 2/2010 | Thornton et al. | |
| 7,682,673 B2 | 3/2010 | Houston et al. | |
| 7,691,124 B2 | 4/2010 | Balgobin | |
| 7,699,056 B2 | 4/2010 | Tran et al. | |
| 7,740,616 B2 | 6/2010 | Smith et al. | |
| 7,771,463 B2 | 8/2010 | Ton et al. | |
| 7,785,343 B2 | 8/2010 | Johnson et al. | |
| 7,785,631 B2 | 8/2010 | Roser et al. | |
| 7,789,860 B2 | 9/2010 | Brady et al. | |
| 7,789,892 B2 | 9/2010 | Johnson et al. | |
| 7,803,177 B2 | 9/2010 | Hartley et al. | |
| 7,854,747 B2 | 12/2010 | Johnson et al. | |
| 7,955,343 B2 | 6/2011 | Makower et al. | |
| 7,967,837 B2 | 6/2011 | Vale | |
| 7,985,250 B2 | 7/2011 | Kaufmann et al. | |
| 7,992,565 B2 | 8/2011 | McGuckin, Jr. et al. | |

(56) References Cited

U.S. PATENT DOCUMENTS

| | | |
|---|---|---|
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 2001/0007946 A1 | 7/2001 | Lenker et al. |
| 2001/0031981 A1 | 10/2001 | Evans et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0123765 A1 | 9/2002 | Sepetka et al. |
| 2002/0143362 A1* | 10/2002 | Macoviak et al. ............ 606/200 |
| 2002/0177855 A1 | 11/2002 | Greene et al. |
| 2002/0198588 A1 | 12/2002 | Armstrong et al. |
| 2003/0114922 A1 | 6/2003 | Iwasaka et al. |
| 2003/0125798 A1 | 7/2003 | Martin |
| 2003/0153972 A1 | 8/2003 | Helmus |
| 2003/0171801 A1 | 9/2003 | Bates |
| 2003/0187474 A1* | 10/2003 | Keegan et al. ............... 606/200 |
| 2003/0187495 A1 | 10/2003 | Cully et al. |
| 2003/0216679 A1 | 11/2003 | Wolf et al. |
| 2003/0229366 A1* | 12/2003 | Reggie et al. ................ 606/158 |
| 2004/0010282 A1 | 1/2004 | Kusleika |
| 2004/0029994 A1 | 2/2004 | Cheng et al. |
| 2004/0055606 A1 | 3/2004 | Hendricksen et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1* | 8/2004 | Hogendijk et al. .......... 623/1.11 |
| 2004/0193141 A1 | 9/2004 | Leopold et al. |
| 2004/0220663 A1* | 11/2004 | Rivelli, Jr. ................... 623/1.22 |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1* | 12/2004 | Allen ........................... 623/1.12 |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0165442 A1 | 7/2005 | Thinnes et al. |
| 2005/0192616 A1 | 9/2005 | Callister et al. |
| 2005/0209675 A1 | 9/2005 | Ton et al. |
| 2005/0288684 A1 | 12/2005 | Aronson et al. |
| 2006/0009798 A1 | 1/2006 | Callister et al. |
| 2006/0052822 A1 | 3/2006 | Mirizzi et al. |
| 2006/0119714 A1 | 6/2006 | Tamura et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1 | 5/2007 | Strecker |
| 2007/0129753 A1 | 6/2007 | Quinn et al. |
| 2007/0135826 A1 | 6/2007 | Zaver et al. |
| 2007/0150045 A1 | 6/2007 | Ferrera |
| 2007/0156224 A1 | 7/2007 | Cioanta et al. |
| 2007/0163601 A1 | 7/2007 | Pollock et al. |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0239191 A1 | 10/2007 | Ramzipoor |
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0086214 A1 | 4/2008 | Hardin et al. |
| 2008/0103522 A1 | 5/2008 | Steingisser et al. |
| 2008/0132906 A1 | 6/2008 | Rasmussen |
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1* | 9/2008 | Dieck et al. ................... 606/157 |
| 2008/0269719 A1 | 10/2008 | Balgobin et al. |
| 2008/0302368 A1 | 12/2008 | McGuckin, Jr. et al. |
| 2009/0005847 A1 | 1/2009 | Adams |
| 2009/0018562 A1 | 1/2009 | Amplatz et al. |
| 2009/0018636 A1 | 1/2009 | Gailloud et al. |
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1 | 3/2009 | Amplatz et al. |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0106235 A1 | 4/2010 | Kariniemi et al. |
| 2010/0114307 A1 | 5/2010 | Agnew et al. |
| 2010/0121370 A1 | 5/2010 | Kariniemi |
| 2010/0174269 A1 | 7/2010 | Tompkins et al. |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0268260 A1 | 10/2010 | Riina et al. |
| 2010/0294282 A1 | 11/2010 | Chu et al. |
| 2010/0312268 A1* | 12/2010 | Belson ........................ 606/200 |
| 2010/0318178 A1 | 12/2010 | Rapaport et al. |
| 2010/0324585 A1 | 12/2010 | Miles et al. |
| 2010/0324586 A1 | 12/2010 | Miles et al. |

(56) References Cited

U.S. PATENT DOCUMENTS

| | | |
|---|---|---|
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0124958 A1 | 5/2011 | Nelson |
| 2011/0125132 A1 | 5/2011 | Krolik et al. |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1 | 12/2011 | Rudakov et al. |
| 2012/0010556 A1 | 1/2012 | Faul et al. |
| 2012/0022572 A1 | 1/2012 | Braun et al. |
| 2012/0083822 A1 | 4/2012 | Anukhin et al. |
| 2012/0089216 A1 | 4/2012 | Rapaport et al. |
| 2012/0095489 A1 | 4/2012 | Rudakov et al. |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0192872 A1 | 8/2012 | Rudakov et al. |
| 2012/0209310 A1 | 8/2012 | Chen et al. |
| 2012/0239077 A1 | 9/2012 | Zaver et al. |
| 2012/0245620 A1 | 9/2012 | Gilson et al. |
| 2012/0245668 A1 | 9/2012 | Kariniemi et al. |
| 2012/0259354 A1 | 10/2012 | Kellett |
| 2012/0277842 A1 | 11/2012 | Kunis |
| 2012/0289988 A1 | 11/2012 | Riina et al. |
| 2012/0289994 A1 | 11/2012 | Larson et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1 | 8/2013 | Kunis |
| 2013/0289714 A1 | 10/2013 | Strauss et al. |
| 2014/0128780 A1 | 5/2014 | Kennedy et al. |
| 2014/0215792 A1 | 8/2014 | Leopold et al. |
| 2014/0222059 A1 | 8/2014 | Leopold et al. |

FOREIGN PATENT DOCUMENTS

| | | |
|---|---|---|
| EP | 1188413 | 3/2002 |
| EP | 1317908 A2 | 6/2003 |
| EP | 1600110 | 11/2005 |
| EP | 1707233 A2 | 10/2006 |
| EP | 1752112 | 2/2007 |
| EP | 1813196 | 8/2007 |
| EP | 1820436 A2 | 8/2007 |
| EP | 1852073 | 11/2007 |
| EP | 2248471 | 11/2010 |
| EP | 2366362 | 9/2011 |
| EP | 2366363 | 9/2011 |
| EP | 2366364 | 9/2011 |
| EP | 2404580 | 1/2012 |
| EP | 2583636 | 4/2013 |
| GB | 2404860 A | 2/2005 |
| GB | 2494820 A | 3/2013 |
| JP | H 07-000405 | 1/1995 |
| JP | 07-18501 | 7/1995 |
| JP | 2006-181015 A | 7/2006 |
| JP | 2010-532180 A | 10/2010 |
| JP | 2012-525859 A | 10/2012 |
| WO | WO-83/00997 | 3/1983 |
| WO | WO-92/14408 | 9/1992 |
| WO | WO-94/00179 A1 | 1/1994 |
| WO | WO-95/24158 | 9/1995 |
| WO | WO-95/25480 A1 | 9/1995 |
| WO | WO-95/32018 | 11/1995 |
| WO | WO-96/18361 | 6/1996 |
| WO | WO-97/13463 | 4/1997 |
| WO | WO-97/13471 | 4/1997 |
| WO | WO-97/27893 | 8/1997 |
| WO | WO-97/27897 | 8/1997 |
| WO | WO-97/27898 | 8/1997 |
| WO | WO-97/31672 | 9/1997 |
| WO | WO-98/08456 | 3/1998 |
| WO | WO-98/31308 | 7/1998 |
| WO | WO-98/31308 A1 | 7/1998 |
| WO | WO-98/34546 | 8/1998 |
| WO | WO-98/46115 A2 | 10/1998 |
| WO | WO-98/46119 | 10/1998 |
| WO | WO-99/12484 | 3/1999 |
| WO | WO-99/23976 | 5/1999 |
| WO | WO-99/25273 | 5/1999 |
| WO | WO-99/44542 A2 | 9/1999 |
| WO | WO-99/48545 | 9/1999 |
| WO | WO-99/49793 | 10/1999 |
| WO | WO-99/49910 A2 | 10/1999 |
| WO | WO-99/62430 | 12/1999 |
| WO | WO-00/09195 | 2/2000 |
| WO | WO-00/16847 | 3/2000 |
| WO | WO-00/27303 A2 | 5/2000 |
| WO | WO-00/67671 | 11/2000 |
| WO | WO-01/32254 | 5/2001 |
| WO | WO-01/64112 A1 | 9/2001 |
| WO | WO-01/80776 | 11/2001 |
| WO | WO-01/80777 A2 | 11/2001 |
| WO | WO-01/89413 A2 | 11/2001 |
| WO | WO-02/03889 | 1/2002 |
| WO | WO-03/001970 A2 | 1/2003 |
| WO | WO-03/073961 | 9/2003 |
| WO | WO-03/073962 | 9/2003 |
| WO | WO-03/101518 | 12/2003 |
| WO | WO-2004/006804 | 1/2004 |
| WO | WO-2004/073557 A2 | 9/2004 |
| WO | WO-2005/020786 A2 | 3/2005 |
| WO | WO-2005/092241 | 10/2005 |
| WO | WO 2005/117755 | 12/2005 |
| WO | WO-2006/017470 A2 | 2/2006 |
| WO | WO-2006/028943 | 3/2006 |
| WO | WO-2006/031602 | 3/2006 |
| WO | WO-2006/034153 A2 | 3/2006 |
| WO | WO-2006/074163 A2 | 7/2006 |
| WO | WO-2006/096342 | 9/2006 |
| WO | WO-2006/111801 A2 | 10/2006 |
| WO | WO-2006/134354 | 12/2006 |
| WO | WO-2007/061927 A2 | 5/2007 |
| WO | WO-2007/070544 A2 | 6/2007 |
| WO | WO-2007/085373 | 8/2007 |
| WO | WO-2007/127351 | 11/2007 |
| WO | WO-2007/149844 A2 | 12/2007 |
| WO | WO-2008/010197 A2 | 1/2008 |
| WO | WO-2008/100790 A2 | 8/2008 |
| WO | WO-2008/112501 A2 | 9/2008 |
| WO | WO-2008/153653 | 12/2008 |
| WO | WO-2009/064618 | 5/2009 |
| WO | WO-2009/077845 A2 | 6/2009 |
| WO | WO-2009/088905 | 7/2009 |
| WO | WO-2009/124288 | 10/2009 |
| WO | WO-2009/126747 | 10/2009 |
| WO | WO-2010/009019 | 1/2010 |
| WO | WO-2010/047644 | 4/2010 |
| WO | WO-2010/047644 A1 | 4/2010 |
| WO | WO-2010/075565 A2 | 7/2010 |
| WO | WO-2010/085344 A1 | 7/2010 |
| WO | WO-2010/096717 | 8/2010 |
| WO | WO-2010/130617 | 11/2010 |
| WO | WO-2010/146581 | 12/2010 |
| WO | WO-2010/148246 A2 | 12/2010 |
| WO | WO-2011/011581 A2 | 1/2011 |

(56) References Cited

FOREIGN PATENT DOCUMENTS

| WO | WO-2011/153304 | | 12/2011 |
|---|---|---|---|
| WO | WO-2011/163157 | A2 | 12/2011 |
| WO | WO-2012/002944 | | 1/2012 |
| WO | WO-2012/040380 | | 3/2012 |
| WO | WO-2012/067724 | | 5/2012 |
| WO | WO-2012/109367 | | 8/2012 |
| WO | WO-2012/111137 | | 8/2012 |
| WO | WO-2012/131672 | A2 | 10/2012 |
| WO | WO-2012/134761 | | 10/2012 |
| WO | WO-2012/135859 | A2 | 10/2012 |
| WO | WO-2012/166804 | | 12/2012 |
| WO | WO-2013/055703 | A1 | 4/2013 |
| WO | WO-2013/059511 | A1 | 4/2013 |
| WO | WO-2013/067299 | | 5/2013 |

OTHER PUBLICATIONS

Berguer et al., Cure by Combination of Operation and Detachable Intravascular Balloon, Ann. Surg. Jul. 1982, pp. 65-68, vol. 196, No. 1.

Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.

DeSouza et al., Embolization with Detachable Balloons—Applications Outside the Head, Clinical Radiology, Apr. 21, 1992, pp. 170-175, vol. 46.

Hawkins et al., The Permeability of Detachable Latex Rubber Balloons—An In Vitro Study, Investigative Radiology, Dec. 1987, pp. 969-972, vol. 22.

Hirai et al., Emergency Balloon Embolization for Carotid Artery Rupture Secondary to Postoperative Infection, Cardiovasc Intervent Radiol, 1996, pp. 50-52, vol. 19.

Kallmes et al., The Use of Hydrocoil for Parent Artery Occlusion, AJNR Am J Neuroradiol, Sep. 2004, pp. 1409-1410, vol. 25.

Kaufman, et al., Detachable Balloon-Modified Reducing Stent to Treat Hepatic Insufficiency After Transjugular Intrahepatic Portosystemic Shunt Creation, J Vasc Interv Radiol., May 2003, pp. 635-638, vol. 14, No. 5.

Luo, Chao-Bao et al., Endovascular Treatment of the Carotid Artery Rupture with Massive Hemorrhage, J. Chin Med Assoc., Mar. 2003.

Makita, et al., Guide-Wire-Directed Detachable Balloon: Clinical Application in Treatment of Varicoceles, Radiology, 1992, pp. 575-577, vol. 183.

Marshall et al., Treatment of Traumatic Renal Arteriovenous Fistulas by Detachable Silicone Balloon Embolization, The Journal of Urology, Aug. 1979, pp. 237-239, vol. 122.

Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.

Pollak et al., Clinical Results of Transvenous Systemic Embolotherapy with a Neuroradiologic Detachable Balloon, Radiology, May 1994, pp. 477-482, vol. 191, No. 2.

Reidy et al., Transcatherer Occlusion of Coronary to Bronchial Anastomosis by Detachable Balloon Combined with Coronary Angioplasty at Same Procedure, Brit Heart J. 1983, pp. 284-287, vol. 49.

Reidy et al., Transcatheter Occlusion of a Blalock-Taussig Shunt with a Detachable Balloon in a Child, Bri Heart Journal, 1983, pp. 101-103, vol. 50.

Ross et al., The Vascular Plug: A New Device for Parent Artery Occlusion, AJNR Am J Neuroradiol, Feb. 2007, pp. 385-386, vol. 28.

Serbinenko, F.A., Balloon Catheterization and Occlusion of Major Cerebral Vessels, J. Neurosurg. Aug. 1974, pp. 125-145, vol. 41.

Tasar, et al., Intrahepatic Arterioportal Fistula and its Treatment with Detachable Balloon and Transcatheter Embolization with Coils and Microspheres, Journal of Clinical Imaging, 2005, pp. 325-330, vol. 29.

Wehman, et al., Giant Cerebral Aneurysms: Endovascular Challenges, Neurosurgery, Nov. 2006, pp. S125-S138, vol. 59, No. 5.

White, et al., Occlusion of Varicoceles with Detachable Balloons, Radiology, May 1981, pp. 327-334, vol. 139.

Serbinenko, F.A., Occlusion by Balooning of Sacular Aneurysms of the Cerebral Arteries, Vopr, Neirokhir, Jul.-Aug. 1974, pp. 8-15, vol. 4.

Serebinko, F.A., Balloon Occlusion of Cavernous Portion of the Carotid Artery as a Method of Treating Carotid Cavity Anastomoses, Vopr. Neirokhir, Nov.-Dec. 1971, pp. 3-9, vol. 6.

Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.

Kadir et al., Therapeutic Embolization of the Kidney with Detachable Silicone Balloons, The Journal of Urology, Jan. 1983, pp. 11-13, vol. 129.

U.S. Appl. No. 13/828,974, filed Mar. 14, 2013.
U.S. Appl. No. 14/044,794, filed Oct. 2, 2013.
U.S. Appl. No. 14/101,171, filed Dec. 9, 2013.

\* cited by examiner

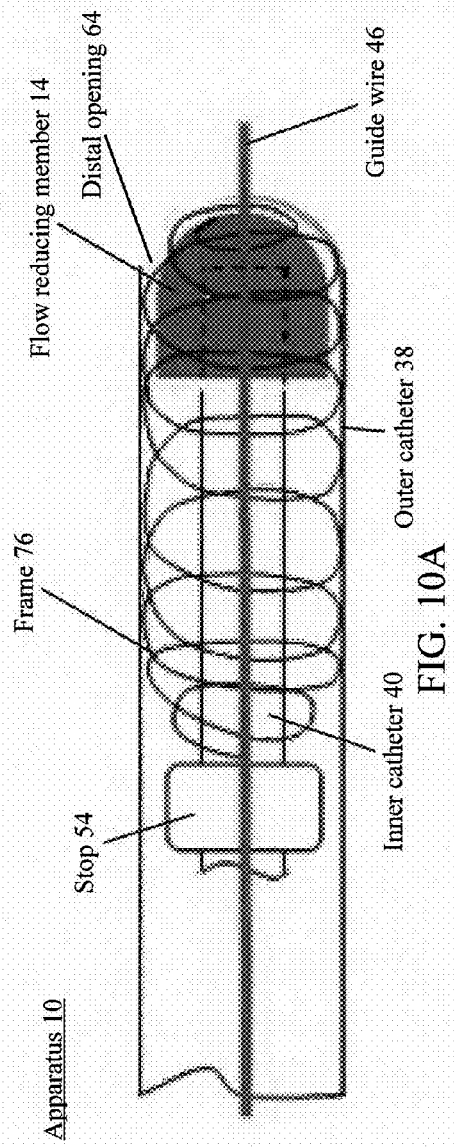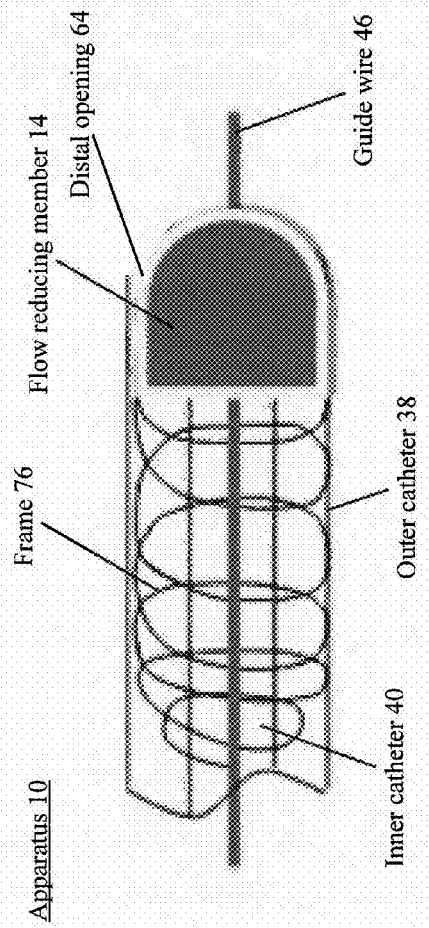

REDUCING FLOW THROUGH A TUBULAR STRUCTURE

FIELD

The present invention generally relates to methods and apparatus for reducing or stopping flow through a tubular structure of a patient.

BACKGROUND

Devices exist for stenting tubular structures in patients. Stents typically maintain patency in tubular structures such as blood vessels. As a result, flow of fluid such as blood through the tubular structures is generally maintained.

SUMMARY

Problems associated with typical devices for occluding flow through tubular structures of patients include inaccurate deployment and positioning of these devices within the tubular structures, as well as having continuous and significant residual flow. These devices, once deployed, do not provide mechanisms allowing for their repositioning and/or removal in a simple manner. Thus, once these devices have been deployed, the devices are typically committed to their initially deployed positions. It is therefore desirable to provide devices that can be used to reduce or stop flow through a tubular structure of a patient, and also allow for their repositioning and/or removal.

According to various embodiments of the subject technology, an apparatus is provided for reducing or stopping flow through a tubular structure of a patient. The apparatus comprises a first elongate member arranged to form a first frame having a distal opening and a proximal opening. The first frame is configured to be positioned within a lumen of the tubular structure. The first frame includes a proximal portion, a distal portion, and a middle portion therebetween. The distal portion is tapered such that an outer cross sectional dimension of the distal opening is less than an outer cross sectional dimension of the middle portion. The first frame is configured to be inverted such that the distal portion moves within and toward the middle portion for removing the first frame from within the lumen. The apparatus also comprises a first flow reducing member coupled to the first frame such that when the first frame is positioned within the lumen, the first flow reducing member substantially reduces or totally obstructs flow of at least one of emboli and fluid flowing through the lumen.

In some embodiments the first elongate member is arranged in a spiral configuration to form the first frame. In some embodiments, the first flow reducing member totally obstructs flow of the at least one of emboli and fluid flowing through the lumen. In some embodiments, the first flow reducing member is coupled to the first frame using surgical suture. In some embodiments, the first frame is further configured to expand from an undeployed configuration to a deployed configuration such that the first frame engages an inner surface of the lumen. The first frame may be expanded with a balloon or may be self expandable.

According to certain embodiments, the proximal portion is tapered such that an outer cross sectional dimension of the proximal opening is less than an outer cross sectional dimension of the middle portion. In some embodiments, the outer cross sectional dimension of the proximal opening is larger than an outer cross sectional dimension of the distal opening.

In some embodiments, the first elongate member comprises at least one of stainless steel, nickel titanium (NiTi), cobalt chromium (CoCr), titanium, a polymer, a polyester based material, a tyrosine based polycarbonate, a polyethylene based material, and Teflon (e.g., including expanded Teflon). The first elongate member may also comprise at least one of polyethylene, polyglicolide, polylactide, c-caprolactone, polycarbonate, hydroxyalkanote, para dioxinine, PLA, PGA, PLLA, PDLLA, PDO, and PCL. In some embodiments, the first elongate member comprises bioabsorbable material.

According to certain embodiments, the first elongate member comprises a substantially rectangular cross section. A length of the rectangular cross section may be between about 0.008 inches and about 0.014 inches and a width of the rectangular cross section may be between about 0.004 inches and about 0.006 inches. Corners of the rectangular cross section may be curved.

In some embodiments, the first frame is coated with biological glue. The biological glue may comprise glue from at least one of crab shells, spider webs, gecko feet, burrowing frogs, mussels, and caulobacter crescentus bacteria.

In some embodiments, the first flow reducing member comprises at least one of a polyurethane and a polyanhidrate. In some embodiments, the first flow reducing member comprises expanded polytetrafluoroethylene (ePTFE). In some embodiments, the first flow reducing member comprises bioabsorbable material. In some embodiments, the first flow reducing member comprises a self sealing material. The first flow reducing member may be configured to facilitate an extension of a guide wire through therethrough. In some embodiments, the first flow reducing member comprises a plurality of pores each having a diameter of between about 5 microns and about 10 microns.

According to certain embodiments, the first flow reducing member is disposed over an exterior of the first frame. The first flow reducing member may be disposed over the distal portion. A hole may be defined in the first flow reducing member. The hole may allow a guide wire to extend therethrough. The first flow reducing member may comprise a portion configured to partially, substantially, or totally block the hole when the guide wire is removed therefrom. Swelling material may be disposed in or on the portion. When fluid contacts the swelling material, the swelling material and the portion may be expanded to substantially or totally block the hole. In some aspects, the portion may comprise a pocket. In some aspects, the swelling material may be comprised of microparticles. In some aspects, the swelling material may comprise hydrogel.

In some embodiments, at least a portion of the first flow reducing member extends from the exterior of the first frame into an interior of the first frame through the distal opening to form a flap in the interior of the first frame. The flap is configured to substantially prevent distal flow through the distal opening and facilitate proximal flow through the distal opening.

In some embodiments, an average thickness of the first flow reducing member is between about 0.0005 inches and about 0.006 inches. In some embodiments, an average thickness of a distal portion of the first flow reducing member is greater than an average thickness of a proximal portion of the first flow reducing member. The average thickness of the distal portion of the first flow reducing member may be between about 0.002 inches and about 0.012 inches and the average thickness of the proximal portion of the first flow reducing member may be between about 0.0005 inches and about 0.006 inches.

In some embodiments, the first flow reducing member is disposed over the distal opening. In some embodiments, the first flow reducing member is disposed over the proximal portion, the middle portion, and the distal portion.

According to certain embodiments, a radio-opaque marker is placed on a first coil of the first frame. An outer cross sectional dimension of the first coil may be less than an outer cross sectional dimension of a second coil of the first frame. The radio-opaque marker may surround an exterior of the first coil. The first coil may be adjacent to a second coil of the first frame. The first flow reducing member may be coupled to the second coil. The radio-opaque marker may comprise a platinum iridium alloy.

In some embodiments, the first flow reducing member is disposed in an interior of the first frame. The first flow reducing member may be coupled to the middle portion. The first flow reducing member may be coupled to a first coil of the first frame such that the first flow reducing member substantially covers an opening through the first coil. A portion of the first elongate member from a first point on the first elongate member to a second point on the first elongate member may form the first coil. The first flow reducing member may be coupled to the first elongate member from the first point on the first elongate member to the second point on the first elongate member. A thickness of the first coil of the first frame measured along an axial dimension of the first frame may be less than a thickness of a second coil of the first frame measured along the axial dimension of the first frame.

In some embodiments, the tubular structure comprises at least one of a blood Vessel, a Fallopian tube, a cervical canal, a vagina, a cervix, a vas deferens, a bronchus, a ureter, a colon, a rectum, an anus, a bio duct, and a pancreatic duct. In some embodiments, the apparatus comprises a retrieving member configured to couple to the distal portion and to retrieve the distal portion toward an interior of the first frame for inverting the first frame. The retrieving member may comprise at least one jaw having a stowed position and a deployed position. The at least one jaw may be configured to expand from the stowed position to the deployed position for coupling to the distal portion. The at least one jaw may comprise a curved portion.

In certain embodiments, the apparatus comprises a tube configured to extend through the distal opening to be positioned at a target site of the patient. The apparatus also comprises a vacuum source configured to apply a vacuum through the tube for removing at least one of emboli and fluid from the target site.

In some embodiments, the apparatus comprises an outer catheter configured to be positioned within the lumen at a first deployment site. The apparatus also comprises an inner catheter disposed within the outer catheter. The first frame is configured to be positioned between the inner catheter and the outer catheter for stowage of the first frame before the first frame is deployed within the lumen.

In some embodiments, the apparatus also comprises one or more threads formed in or on an outer surface of the inner catheter such that the first elongate member wraps around the one or more threads for securing the first elongate member to the inner catheter. In some embodiments, the apparatus comprises one or more blocks disposed on an outer surface of the inner catheter such that the first elongate member wraps around the one or more blocks for securing the first elongate member to the inner catheter. The one or more blocks may comprise electroactive polymer (EAP) and may be configured to swell when electric signals are applied to the one or more blocks. The first elongate member wrapped around the one or more blocks may be substantially locked to the one or more blocks when the electric signals are applied.

In some embodiments, the inner catheter comprises a hole configured such that a proximal tip of the first elongate member extends through the hole from an exterior of the inner catheter into an interior of the inner catheter for securing the first frame to the inner catheter. In some embodiments, the inner catheter comprises a groove configured such that a proximal tip of the first elongate member is disposed in the groove for securing the first frame to the inner catheter.

In certain embodiments, the first flow reducing member is disposed over the distal portion. The distal portion and the first flow reducing member extend distally beyond a distal opening of the outer catheter such that when the outer catheter is moved within the lumen to the first deployment site, the distally extended portion of the first flow reducing member is configured to engage a wall of the lumen to reduce friction.

In some embodiments, the apparatus comprises a first stop disposed between the outer catheter and the inner catheter. The first stop is coupled to an inner surface of the outer catheter and is disposed proximal the first frame when the first frame is positioned between the inner catheter and the outer catheter. The apparatus also comprises a second stop disposed between the outer catheter and the inner catheter. The second stop is coupled to an outer surface of the inner catheter and is disposed proximal the first stop. When the inner catheter is shifted distally relative to the outer catheter for deploying the first frame, the second stop engages the first stop to substantially prevent the inner catheter from further distal shifting relative to the outer catheter. In some embodiments, the second stop comprises a groove configured such that a proximal tip of the first elongate member is disposed in the groove for securing the first frame to the inner catheter.

In some embodiments, the apparatus comprises a stop disposed between the outer catheter and the inner catheter. The stop is further disposed proximal the first frame when the first frame is positioned between the inner catheter and the outer catheter. The stop is configured to substantially prevent the first frame from moving proximally relative to at least one of the outer catheter and the inner catheter. In some embodiments, the stop comprises a groove configured such that a proximal tip of the first elongate member is disposed in the groove for securing the first frame to the inner catheter.

In some embodiments, the apparatus also comprises a guide wire configured to extend through the inner catheter and the distal opening of the first frame. In some embodiments, the apparatus also comprises a second elongate member arranged in a spiral configuration to form a second frame having a distal opening and a proximal opening. The second frame is configured to be positioned within the lumen. The second frame includes a proximal portion, a distal portion, and a middle portion therebetween. The distal portion of the second frame is tapered such that an outer cross sectional dimension of the distal opening of the second frame is less than an outer cross sectional dimension of the middle portion of the second frame. The second frame is configured to be inverted such that the distal portion of the second frame moves within and toward the middle portion of the second frame for removing the second frame from within the lumen. The apparatus also comprises a second flow reducing member coupled to the second frame such that when the second frame is positioned within the lumen, the second flow reducing member substantially reduces or totally obstructs flow of at least one of emboli and fluid flowing through the lumen.

In some embodiments, the second frame is configured to be positioned between the outer catheter and the guide wire for stowage of the second frame before the second frame is deployed within the lumen. The apparatus also comprises one or more threads formed in or on an outer surface of the guide wire such that the second elongate member wraps around the one or more threads for securing the second elongate member to the guide wire. In some embodiments, the apparatus comprises one or more blocks disposed on an outer surface of the guide wire such that the second elongate member wraps around the one or more blocks for securing the second elongate member to the guide wire. The one or more blocks may comprise electroactive polymer (EAP) and are configured to swell when electric signals are applied to the one or more blocks. The second elongate member wrapped around the one or more blocks may be substantially locked to the one or more blocks when the electric signals are applied.

In some embodiments, the first flow reducing member is disposed over the distal portion of the first frame and the second flow reducing member is disposed over the proximal portion of the second frame. In some embodiments, the first flow reducing member is disposed over the distal portion of the first frame and the second flow reducing member is disposed over the distal portion of the second frame.

According to certain embodiments, the guide wire is configured to shift distally relative to the outer catheter until the second frame extends beyond a distal opening of the outer catheter into the first deployment site for deploying the second frame from the outer catheter. The outer catheter is configured to be positioned within the lumen at a second deployment site for deploying the first frame at the second deployment site. The inner catheter is configured to shift distally relative to the outer catheter until the first frame extends beyond the distal opening of the outer catheter into the second deployment site.

In some embodiments, the guide wire is configured to shift distally relative to the outer catheter until a portion of the second frame extends beyond a distal opening of the outer catheter into the first deployment site for partially deploying the second frame from the outer catheter. The guide wire is configured to shift proximally relative to the outer catheter until the portion of the second frame is retracted proximally into the outer catheter for retracting the second frame into the outer catheter. The outer catheter is configured to be positioned within the lumen at a second deployment site for deploying the second frame at the second deployment site. The guide wire is configured to shift distally relative to the outer catheter until the second frame extends beyond the distal opening of the outer catheter into the second deployment site.

In some embodiments, the inner catheter is configured to shift distally relative to the outer catheter until the first frame extends beyond a distal opening of the outer catheter into the first deployment site for deploying the first frame from the outer catheter. In some embodiments, the inner catheter is configured to shift distally relative to the outer catheter until a portion of the first frame extends beyond a distal opening of the outer catheter into the first deployment site for partially deploying the first frame from the outer catheter. The inner catheter is configured to shift proximally relative to the outer catheter until the portion of the first frame is retracted proximally into the outer catheter for retracting the first frame into the outer catheter. The outer catheter is configured to be positioned within the lumen at a second deployment site for deploying the first frame at the second deployment site. The inner catheter is configured to shift distally relative to the outer catheter until the first frame extends beyond the distal opening of the outer catheter into the second deployment site for deploying the first frame from the outer catheter.

In some embodiments, the inner catheter comprises a proximal handle. The first frame and the first flow reducing member are deployed from the outer catheter by shifting the proximal handle and the inner catheter distally relative to the outer catheter until the first frame and the first flow reducing member extend beyond a distal opening of the outer catheter into the lumen. In some embodiments, the apparatus comprises a security block coupled to the proximal handle. The security block is configured to substantially prevent the proximal handle and the inner catheter from shifting distally relative to the outer catheter.

According to various embodiments of the subject technology, a method for reducing or stopping flow through a tubular structure of a patient is provided. The method comprises positioning a first elongate member within a lumen of the tubular structure. The first elongate member is arranged to form a first frame having a distal opening and a proximal opening. The first frame includes a proximal portion, a distal portion, and a middle portion therebetween. The distal portion is tapered such that an outer cross sectional dimension of the distal opening is less than an outer cross sectional dimension of the middle portion. The method also comprises substantially reducing or totally obstructing, with a first flow reducing member coupled to the first frame, flow of at least one of emboli and fluid flowing through the lumen. The method also comprises removing the first frame from within the lumen by inverting the first frame such that the distal portion moves within and toward the middle portion.

In some embodiments the first elongate member is arranged in a spiral configuration to form the first frame. In some embodiments, the method comprises totally obstructing, with the first flow reducing member coupled to the first frame, flow of the at least one of emboli and fluid flowing through the lumen. In some embodiments, the first flow reducing member is coupled to the first frame using surgical suture. In some embodiments, the method comprises expanding the first frame from an undeployed configuration to a deployed configuration such that the first frame engages an inner surface of the lumen. The first frame may be expanded with a balloon or may be self-expandable.

According to certain embodiments, the proximal portion is tapered such that an outer cross sectional dimension of the proximal opening is less than the outer cross sectional dimension of the middle portion. In some embodiments, the outer cross sectional dimension of the proximal opening is larger than an outer cross sectional dimension of the distal opening.

In some embodiments, the first elongate member comprises at least one of stainless steel, nickel titanium (NiTi), cobalt chromium (CoCr), titanium, a polymer, a polyester based material, a tyrosine based polycarbonate, a polyethylene based material, and Teflon (e.g., including expanded Teflon). The first elongate member may also comprise at least one of polyethylene, polyglicolide, polylactide, ε-caprolactone, polycarbonate, hydroxyalkanote, para dioxinine, PLA, PGA, PLLA, PDLLA, PDO, and PCL. In some embodiments, the first elongate member comprises bioabsorbable material.

According to certain embodiments, the first elongate member comprises a substantially rectangular cross section. A length of the rectangular cross section may be between about 0.008 inches and about 0.014 inches and a width of the rectangular cross section may be between about 0.004 inches and about 0.006 inches. Corners of the rectangular cross section may be curved.

In some embodiments, the first frame is coated with biological glue. The biological glue may comprise glue from at least one of crab shells, spider webs, gecko feet, burrowing frogs, mussels, and caulobacter crescentus bacteria.

In some embodiments, the first flow reducing member comprises at least one of a polyurethane and a polyanhidrate. In some embodiments, the first flow reducing member comprises expanded polytetrafluoroethylene (ePTFE). In some embodiments, the first flow reducing member comprises bioabsorbable material. In some embodiments, the first flow reducing member comprises a self sealing material. The first flow reducing member may be configured to facilitate an extension of a guide wire through therethrough. In some embodiments, the first flow reducing member comprises a plurality of pores each having a diameter of between about 5 microns and about 10 microns. In some embodiments, an average thickness of the first flow reducing member is between about 0.0005 inches and about 0.006 inches.

According to certain embodiments, the first flow reducing member is disposed over an exterior of the first frame. The first flow reducing member may be disposed over the distal portion. A hole may be defined in the first flow reducing member. The hole may allow a guide wire to extend therethrough. The first flow reducing member may comprise a portion configured to partially, substantially, or totally block the hole when the guide wire is removed therefrom. Swelling material may be disposed in or on the portion. When fluid contacts the swelling material, the swelling material and the portion may be expanded to substantially or totally block the hole. In some aspects, the portion may comprise a pocket. In some aspects, the swelling material may be comprised of microparticles. In some aspects, the swelling material may comprise hydrogel.

In some embodiments, at least a portion of the first flow reducing member extends from the exterior of the first frame into an interior of the first frame through the distal opening to form a flap in the interior of the first frame. In some embodiments, the substantially reducing or totally obstructing comprises: substantially preventing, with the flap, distal flow through the distal opening; and facilitating, with the flap, proximal flow through the distal opening.

In some embodiments, an average thickness of the first flow reducing member is between about 0.0005 inches and about 0.006 inches. In some embodiments, an average thickness of a distal portion of the first flow reducing member is greater than an average thickness of a proximal portion of the first flow reducing member. The average thickness of the distal portion of the first flow reducing member may be between about 0.002 inches and about 0.012 inches and the average thickness of the proximal portion of the first flow reducing member may be between about 0.0005 inches and about 0.006 inches.

In some embodiments, the first flow reducing member is disposed over the distal opening. In some embodiments, the first flow reducing member is disposed over the proximal portion, the middle portion, and the distal portion.

According to certain embodiments, a radio-opaque marker is placed on a first coil of the first frame. An outer cross sectional dimension of the first coil may be less than an outer cross sectional dimension of a second coil of the first frame. The radio-opaque marker may surround an exterior of the first coil. The first coil may be adjacent to a second coil of the first frame. The first flow reducing member may be coupled to the second coil. The radio-opaque marker may comprise a platinum iridium alloy.

In some embodiments, the first flow reducing member is disposed in an interior of the first frame. The first flow reducing member may be coupled to the middle portion. The first flow reducing member may be coupled to a first coil of the first frame such that the first flow reducing member substantially covers an opening through the first coil. A portion of the first elongate member from a first point on the first elongate member to a second point on the first elongate member may form the first coil. The first flow reducing member may be coupled to the first elongate member from the first point on the first elongate member to the second point on the first elongate member. A thickness of the first coil of the first frame measured along an axial dimension of the first frame may be less than a thickness of a second coil of the first frame measured along the axial dimension of the first frame.

In some embodiments, the tubular structure comprises at least one of a blood vessel, a Fallopian tube, a cervical canal, a vagina, a cervix, a vas deferens, a bronchus, a ureter, a colon, a rectum, an anus, a bio duct, and a pancreatic duct. In some embodiments, the removing comprises: coupling a retrieving member to the distal portion; and retrieving, with the retrieving member, the distal portion toward an interior of the first frame for inverting the first frame. The retrieving member may comprise at least one jaw having a stowed position and a deployed position. The method may further comprise expanding the at least one jaw from the stowed position to the deployed position for coupling to the distal portion. The at least one jaw may comprise a curved portion.

In some embodiments, the method further comprises extending a tube through the distal opening to position the tube at a target site of the patient. The method also comprises applying, with a vacuum source, a vacuum through the tube for removing at least one of emboli and fluid from the target site.

In some embodiments, the method further comprises positioning an outer catheter within the lumen at a first deployment site. An inner catheter is disposed within the outer catheter. The first frame is configured to be positioned between the inner catheter and the outer catheter for stowage of the first frame before the first frame is deployed within the lumen.

In some embodiments, one or more threads are formed in or on an outer surface of the inner catheter such that the first elongate member wraps around the one or more threads for securing the first elongate member to the inner catheter. In some embodiments, one or more blocks are disposed on an outer surface of the inner catheter such that the first elongate member wraps around the one or more blocks for securing the first elongate member to the inner catheter. The one or more blocks may comprise electroactive polymer (EAP) and may be configured to swell when electric signals are applied to the one or more blocks. The first elongate member wrapped around the one or more blocks may be substantially locked to the one or more blocks when the electric signals are applied. In some embodiments, the method further comprises applying electric signals to the one or more blocks. The first elongate member wrapped around the one or more blocks may be substantially locked to the one or more blocks when the electric signals are applied.

In some embodiments, the inner catheter comprises a hole configured such that a proximal tip of the first elongate member extends through the hole from an exterior of the inner catheter into an interior of the inner catheter for securing the first frame to the inner catheter. In some embodiments, the inner catheter comprises a groove configured such that a proximal tip of the first elongate member is disposed in the groove for securing the first frame to the inner catheter.

In certain embodiments, the first flow reducing member is disposed over the distal portion. In some embodiments, the distal portion and the first flow reducing member extend distally beyond a distal opening of the outer catheter. In some embodiments, the positioning the outer catheter comprises moving the outer catheter within the lumen to the first deployment site. In some embodiments, the method further comprises engaging, with the distally extended portion of the first flow reducing member, a wall of the lumen to reduce friction.

In some embodiments, a first stop is disposed between the outer catheter and the inner catheter. The first stop is coupled to an inner surface of the outer catheter and is disposed proximal the first frame when the first frame is positioned between the inner catheter and the outer catheter. A second stop is disposed between the outer catheter and the inner catheter. The second stop is coupled to an outer surface of the inner catheter and is disposed proximal the first stop. When the inner catheter is shifted distally relative to the outer catheter for deploying the first frame, the second stop engages the first stop to substantially prevent the inner catheter from further distal shifting relative to the outer catheter. In some embodiments, the second stop comprises a groove configured such that a proximal tip of the first elongate member is disposed in the groove for securing the first frame to the inner catheter.

In some embodiments, a stop is disposed between the outer catheter and the inner catheter. The stop is further disposed proximal the first frame when the first frame is positioned between the inner catheter and the outer catheter. The method comprises substantially preventing, with the stop, the first frame from moving proximally relative to at least one of the outer catheter and the inner catheter. In some embodiments, the stop comprises a groove configured such that a proximal tip of the first elongate member is disposed in the groove for securing the first frame to the inner catheter.

In some embodiments, a guide wire extends through the inner catheter and the distal opening of the first frame. In some embodiments, the method further comprises positioning a second elongate member within the lumen. The second elongate member is arranged in a spiral configuration to form a second frame having a distal opening and a proximal opening. The second frame includes a proximal portion, a distal portion, and a middle portion therebetween. The distal portion of the second frame is tapered such that an outer cross sectional dimension of the distal opening of the second frame is less than an outer cross sectional dimension of the middle portion of the second frame. The method also comprises substantially reducing or totally obstructing, with a second flow reducing member coupled to the second frame, flow of at least one of emboli and fluid flowing through the lumen. The method also comprises removing the second frame from within the lumen by inverting the second frame such that the distal portion of the second frame moves within and toward the middle portion of the second frame.

In some embodiments, the second frame is configured to be positioned between the outer catheter and the guide wire for stowage of the second frame before the second frame is deployed within the lumen. In some embodiments, the guide wire comprises one or more threads such that the second elongate member wraps around the one or more threads for securing the second elongate member to the guide wire. In some embodiments, one or more blocks is disposed on an outer surface of the guide wire such that the second elongate member wraps around the one or more blocks for securing the second elongate member to the guide wire. The one or more blocks may comprise electroactive polymer (EAP) and are configured to swell when electric signals are applied to the one or more blocks. In some embodiments, the method further comprises applying electric signals to the one or more blocks. The second elongate member wrapped around the one or more blocks may be substantially locked to the one or more blocks when the electric signals are applied.

In some embodiments, the first flow reducing member is disposed over the distal portion of the first frame and the second flow reducing member is disposed over the proximal portion of the second frame. In some embodiments, the first flow reducing member is disposed over the distal portion of the first frame and the second flow reducing member is disposed over the distal portion of the second frame.

In some embodiments, the method further comprises deploying the second frame from the outer catheter by shifting the guide wire distally relative to the outer catheter until the second frame extends beyond a distal opening of the outer catheter into the first deployment site. The method also comprises positioning the outer catheter within the lumen at a second deployment site for deploying the first frame at the second deployment site. The method also comprises deploying the first frame from the outer catheter by shifting the inner catheter distally relative to the outer catheter until the first frame extends beyond the distal opening of the outer catheter into the second deployment site.

In some embodiments, the method further comprises partially deploying the second frame from the outer catheter by shifting the guide wire distally relative to the outer catheter until a portion of the second frame extends beyond a distal opening of the outer catheter into the first deployment site. The method also comprises retracting the second frame into the outer catheter by shifting the guide wire proximally relative to the outer catheter until the portion of the second frame is retracted proximally into the outer catheter. The method also comprises positioning the outer catheter within the lumen at a second deployment site for deploying the second frame at the second deployment site. The method also comprises deploying the second frame from the outer catheter by shifting the guide wire distally relative to the outer catheter until the second frame extends beyond the distal opening of the outer catheter into the second deployment site.

In some embodiments, the method further comprises deploying the first frame from the outer catheter by shifting the inner catheter distally relative to the outer catheter until the first frame extends beyond a distal opening of the outer catheter into the first deployment site. In some embodiments, the method comprises partially deploying the first frame from the outer catheter by shifting the inner catheter distally relative to the outer catheter until a portion of the first frame extends beyond a distal opening of the outer catheter into the first deployment site. The method also comprises retracting the first frame into the outer catheter by shifting the inner catheter proximally relative to the outer catheter until the portion of the first frame is retracted proximally into the outer catheter. The method also comprises positioning the outer catheter within the lumen at a second deployment site of the lumen for deploying the first frame at the second deployment site. The method also comprises deploying the first frame from the outer catheter by shifting the inner catheter distally relative to the outer catheter until the first frame extends beyond the distal opening of the outer catheter into the second deployment site.

In some embodiments, the inner catheter comprises a proximal handle. In some embodiments, the method further comprises deploying the first frame and the first flow reducing member from the outer catheter by shifting the proximal handle and the inner catheter distally relative to the outer catheter until the first frame and the first flow reducing member extend beyond a distal opening of the outer catheter into the lumen. In some embodiments, the method further comprises substantially preventing, with a security block coupled to the proximal handle, the proximal handle and the inner catheter from shifting distally relative to the outer catheter.

According to various embodiments of the subject technology, a method for reducing or stopping flow through a tubular structure of a patient is provided. The method comprises positioning an outer catheter within a lumen of the tubular structure at a first deployment site. An inner catheter is disposed within the outer catheter. A first elongate member is positioned between the inner catheter and the outer catheter. The first elongate member is arranged to form a first frame having a distal opening and a proximal opening. The first frame includes a proximal portion, a distal portion, and a middle portion therebetween. The distal portion is tapered such that an outer cross sectional dimension of the distal opening is less than an outer cross sectional dimension of the middle portion. The method also comprises partially deploying the first frame from the outer catheter by shifting the inner catheter distally relative to the outer catheter until a portion of the first frame extends beyond a distal opening of the outer catheter into the first deployment site. The method also comprises retracting the first frame into the outer catheter by shifting the inner catheter proximally relative to the outer catheter until the portion of the first frame is retracted proximally into the outer catheter. The method also comprises positioning the outer catheter within the lumen at a second deployment site for deploying the first frame at the second deployment site. The method also comprises deploying the first frame from the outer catheter by shifting the inner catheter distally relative to the outer catheter until the first frame extends beyond the distal opening of the outer catheter into the second deployment site. The method also comprises substantially reducing or totally obstructing, with a first flow reducing member coupled to the first frame, flow of at least one of emboli and fluid flowing through the lumen.

In some embodiments the first elongate member is arranged in a spiral configuration to form the first frame. In some embodiments, the method comprises totally obstructing, with the first flow reducing member coupled to the first frame, flow of the at least one of emboli and fluid flowing through the lumen. In some embodiments, the first flow reducing member is coupled to the first frame using surgical suture. In some embodiments, the method comprises expanding the first frame from an undeployed configuration to a deployed configuration such that the first frame engages an inner surface of the lumen. The first frame may be expanded with a balloon or may be self expandable.

According to certain embodiments, the proximal portion is tapered such that an outer cross sectional dimension of the proximal opening is less than the outer cross sectional dimension of the middle portion. In some embodiments, the outer cross sectional dimension of the proximal opening is larger than an outer cross sectional dimension of the distal opening.

In some embodiments, the first elongate member comprises at least one of stainless steel, nickel titanium (NiTi), cobalt chromium (CoCr), titanium, a polymer, a polyester based material, a tyrosine based polycarbonate, a polyethylene based material, and Teflon (e.g., including expanded Teflon). The first elongate member may also comprise at least one of polyethylene, polyglicolide, polylactide, c-caprolactone, polycarbonate, hydroxyalkanote, para dioxinine, PLA, PGA, PLLA, PDLLA, PDO, and PCL. In some embodiments, the first elongate member comprises bioabsorbable material.

According to certain embodiments, the first elongate member comprises a substantially rectangular cross section. A length of the rectangular cross section may be between about 0.008 inches and about 0.014 inches and a width of the rectangular cross section may be between about 0.004 inches and about 0.006 inches. Corners of the rectangular cross section may be curved.

In some embodiments, the first frame is coated with biological glue. The biological glue may comprise glue from at least one of crab shells, spider webs, gecko feet, burrowing frogs, mussels, and caulobacter crescentus bacteria.

In some embodiments, the first flow reducing member comprises at least one of a polyurethane and a polyanhidrate. In some embodiments, the first flow reducing member comprises expanded polytetrafluoroethylene (ePTFE). In some embodiments, the first flow reducing member comprises bioabsorbable material. In some embodiments, the first flow reducing member comprises a self sealing material. The first flow reducing member may be configured to facilitate an extension of a guide wire through therethrough. In some embodiments, the first flow reducing member comprises a plurality of pores each having a diameter of between about 5 microns and about 10 microns. In some embodiments, an average thickness of the first flow reducing member is between about 0.0005 inches and about 0.006 inches.

According to certain embodiments, the first flow reducing member is disposed over an exterior of the first frame. The first flow reducing member may be disposed over the distal portion. A hole may be defined in the first flow reducing member. The hole may allow a guide wire to extend therethrough. The first flow reducing member may comprise a portion configured to partially, substantially, or totally block the hole when the guide wire is removed therefrom. Swelling material may be disposed in or on the portion. When fluid contacts the swelling material, the swelling material and the portion may be expanded to substantially or totally block the hole. In some aspects, the portion may comprise a pocket. In some aspects, the swelling material may be comprised of microparticles. In some aspects, the swelling material may comprise hydrogel.

In some embodiments, at least a portion of the first flow reducing member extends from the exterior of the first frame into an interior of the first frame through the distal opening to form a flap in the interior of the first frame. In some embodiments, the substantially reducing or totally obstructing comprises: substantially preventing, with the flap, distal flow through the distal opening; and facilitating, with the flap, proximal flow through the distal opening.

In some embodiments, an average thickness of the first flow reducing member is between about 0.0005 inches and about 0.006 inches. In some embodiments, an average thickness of a distal portion of the first flow reducing member is greater than an average thickness of a proximal portion of the first flow reducing member. The average thickness of the distal portion of the first flow reducing member may be between about 0.002 inches and about 0.012 inches and the average thickness of the proximal portion of the first flow reducing member may be between about 0.0005 inches and about 0.006 inches.

In some embodiments, the first flow reducing member is disposed over the distal opening. In some embodiments, the first flow reducing member is disposed over the proximal portion, the middle portion, and the distal portion.

According to certain embodiments, a radio-opaque marker is placed on a first coil of the first frame. An outer cross sectional dimension of the first coil may be less than an outer cross sectional dimension of a second coil of the first frame. The radio-opaque marker may surround an exterior of the first coil. The first coil may be adjacent to a second coil of the first frame. The first flow reducing member may be coupled to the second coil. The radio-opaque marker may comprise a platinum iridium alloy.

In some embodiments, the first flow reducing member is disposed in an interior of the first frame. The first flow reducing member may be coupled to the middle portion. The first flow reducing member may be coupled to a first coil of the first frame such that the first flow reducing member substantially covers an opening through the first coil. A portion of the first elongate member from a first point on the first elongate member to a second point on the first elongate member may form the first coil. The first flow reducing member may be coupled to the first elongate member from the first point on the first elongate member to the second point on the first elongate member. A thickness of the first coil of the first frame measured along an axial dimension of the first frame may be less than a thickness of a second coil of the first frame measured along the axial dimension of the first frame.

In some embodiments, the tubular structure comprises at least one of a blood vessel, a Fallopian tube, a cervical canal, a vagina, a cervix, a vas deferens, a bronchus, a ureter, a colon, a rectum, an anus, a bio duct, and a pancreatic duct. In some embodiments, the removing comprises: coupling a retrieving member to the distal portion; and retrieving, with the retrieving member, the distal portion toward an interior of the first frame for inverting the first frame. The retrieving member may comprise at least one jaw having a stowed position and a deployed position. The method may further comprise expanding the at least one jaw from the stowed position to the deployed position for coupling to the distal portion. The at least one jaw may comprise a curved portion.

In some embodiments, the method further comprises extending a tube through the distal opening to position the tube at a target site of the patient. The method also comprises applying, with a vacuum source, a vacuum through the tube for removing at least one of emboli and fluid from the target site.

In some embodiments, one or more threads are formed in or on an outer surface of the inner catheter such that the first elongate member wraps around the one or more threads for securing the first elongate member to the inner catheter. In some embodiments, one or more blocks are disposed on an outer surface of the inner catheter such that the first elongate member wraps around the one or more blocks for securing the first elongate member to the inner catheter. The one or more blocks may comprise electroactive polymer (EAP) and may be configured to swell when electric signals are applied to the one or more blocks. The first elongate member wrapped around the one or more blocks may be substantially locked to the one or more blocks when the electric signals are applied. In some embodiments, the method further comprises applying electric signals to the one or more blocks. The first elongate member wrapped around the one or more blocks may be substantially locked to the one or more blocks when the electric signals are applied.

In some embodiments, the inner catheter comprises a hole configured such that a proximal tip of the first elongate member extends through the hole from an exterior of the inner catheter into an interior of the inner catheter for securing the first frame to the inner catheter. In some embodiments, the inner catheter comprises a groove configured such that a proximal tip of the first elongate member is disposed in the groove for securing the first frame to the inner catheter.

In certain embodiments, the first flow reducing member is disposed over the distal portion. In some embodiments, the distal portion and the first flow reducing member extend distally beyond a distal opening of the outer catheter. In some embodiments, the positioning the outer catheter comprises moving the outer catheter within the lumen to the first deployment site. In some embodiments, the method further comprises engaging, with the distally extended portion of the first flow reducing member, a wall of the lumen to reduce friction.

In some embodiments, a first stop is disposed between the outer catheter and the inner catheter. The first stop is coupled to an inner surface of the outer catheter and is disposed proximal the first frame when the first frame is positioned between the inner catheter and the outer catheter. A second stop is disposed between the outer catheter and the inner catheter. The second stop is coupled to an outer surface of the inner catheter and is disposed proximal the first stop. When the inner catheter is shifted distally relative to the outer catheter for deploying the first frame, the second stop engages the first stop to substantially prevent the inner catheter from further distal shifting relative to the outer catheter. In some embodiments, the second stop comprises a groove configured such that a proximal tip of the first elongate member is disposed in the groove for securing the first frame to the inner catheter.

In some embodiments, a stop is disposed between the outer catheter and the inner catheter. The stop is further disposed proximal the first frame when the first frame is positioned between the inner catheter and the outer catheter. The method comprises substantially preventing, with the stop, the first frame from moving proximally relative to at least one of the outer catheter and the inner catheter. In some embodiments, the stop comprises a groove configured such that a proximal tip of the first elongate member is disposed in the groove for securing the first frame to the inner catheter.

In some embodiments, a guide wire extends through the inner catheter and the distal opening of the first frame. In some embodiments, the method further comprises positioning a second elongate member within the lumen. The second elongate member is arranged in a spiral configuration to form a second frame having a distal opening and a proximal opening. The second frame includes a proximal portion, a distal portion, and a middle portion therebetween. The distal portion of the second frame is tapered such that an outer cross sectional dimension of the distal opening of the second frame is less than an outer cross sectional dimension of the middle portion of the second frame. The method also comprises substantially reducing or totally obstructing, with a second flow reducing member coupled to the second frame, flow of at least one of emboli and fluid flowing through the lumen. The method also comprises removing the second frame from within the lumen by inverting the second frame such that the distal portion of the second frame moves within and toward the middle portion of the second frame.

In some embodiments, the second frame is configured to be positioned between the outer catheter and the guide wire for stowage of the second frame before the second frame is deployed within the lumen. In some embodiments, the guide wire comprises one or more threads such that the second elongate member wraps around the one or more threads for securing the second elongate member to the guide wire. In some embodiments, one or more blocks is disposed on an outer surface of the guide wire such that the second elongate member wraps around the one or more blocks for securing the second elongate member to the guide wire. The one or more blocks may comprise electroactive polymer (EAP) and are configured to swell when electric signals are applied to the one or more blocks. In some embodiments, the method further comprises applying electric signals to the one or more blocks. The second elongate member wrapped around the one or more blocks may be substantially locked to the one or more blocks when the electric signals are applied.

In some embodiments, the first flow reducing member is disposed over the distal portion of the first frame and the second flow reducing member is disposed over the proximal portion of the second frame. In some embodiments, the first flow reducing member is disposed over the distal portion of the first frame and the second flow reducing member is disposed over the distal portion of the second frame.

In some embodiments, the method further comprises deploying the second frame from the outer catheter by shifting the guide wire distally relative to the outer catheter until the second frame extends beyond a distal opening of the outer catheter into the first deployment site.

In some embodiments, the method further comprises partially deploying the second frame from the outer catheter by shifting the guide wire distally relative to the outer catheter until a portion of the second frame extends beyond a distal opening of the outer catheter into a third deployment site. The method also comprises retracting the second frame into the outer catheter by shifting the guide wire proximally relative to the outer catheter until the portion of the second frame is retracted proximally into the outer catheter. The method also comprises positioning the outer catheter within the lumen at a fourth deployment site for deploying the second frame at the fourth deployment site. The method also comprises deploying the second frame from the outer catheter by shifting the guide wire distally relative to the outer catheter until the second frame extends beyond the distal opening of the outer catheter into the fourth deployment site.

In some embodiments, the inner catheter comprises a proximal handle. In some embodiments, the method further comprises deploying the first frame and the first flow reducing member from the outer catheter by shifting the proximal handle and the inner catheter distally relative to the outer catheter until the first frame and the first flow reducing member extend beyond a distal opening of the outer catheter into the lumen. In some embodiments, the method further comprises substantially preventing, with a security block coupled to the proximal handle, the proximal handle and the inner catheter from shifting distally relative to the outer catheter.

Additional features and advantages of the invention will be set forth in the description below, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate aspects of the invention and together with the description serve to explain the principles of the invention.

FIGS. 10A and 10B illustrate an example of a frame and a flow reducing member positioned within an outer catheter, in accordance with various embodiments of the subject technology.

DETAILED DESCRIPTION

In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail so as not to obscure the present invention.

Figure 1:
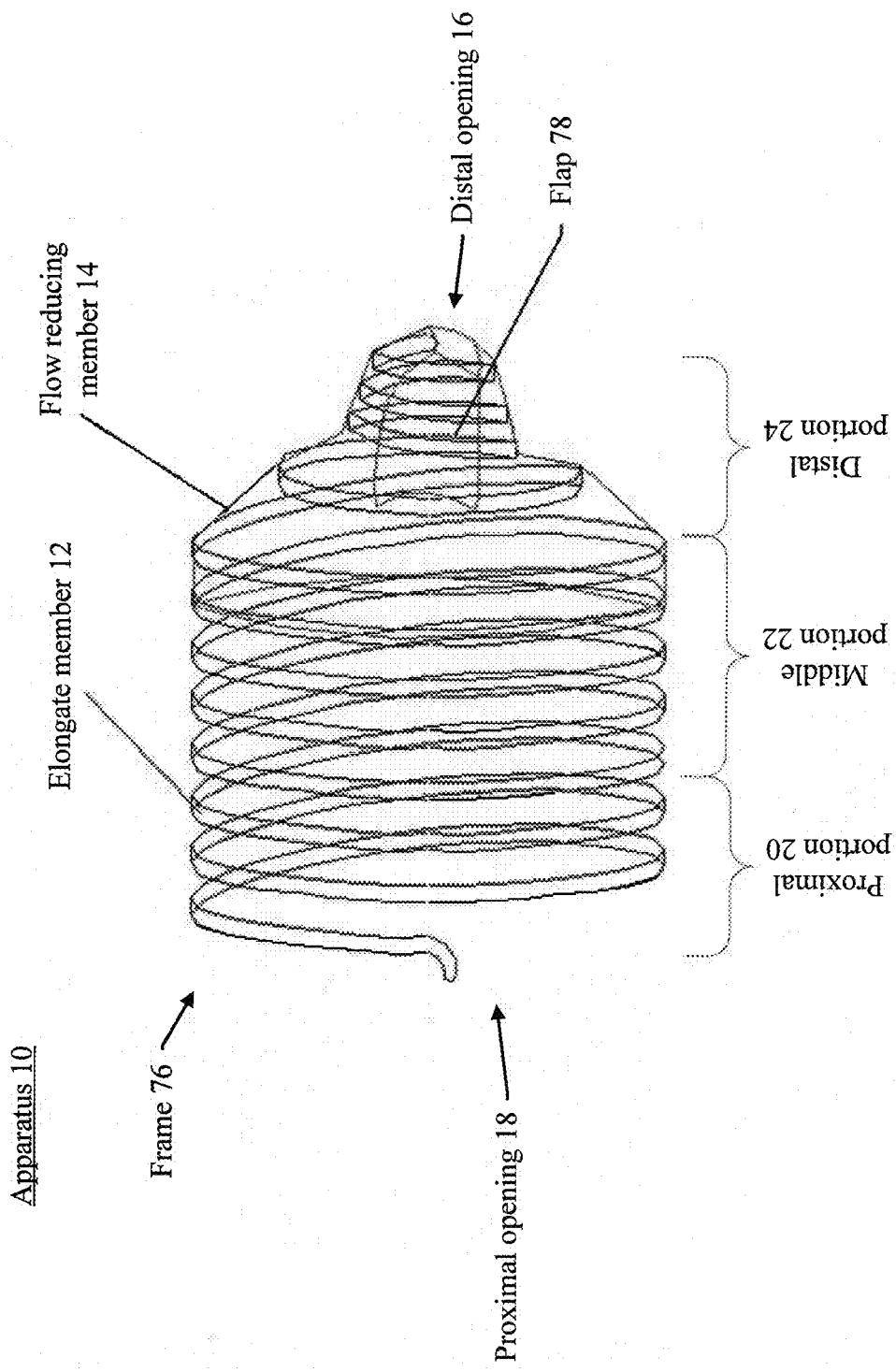
FIG. 1 illustrates an example of an apparatus for reducing or stopping flow through a tubular structure of a patient, in accordance with various embodiments of the subject technology.

FIG. 1 illustrates an example of apparatus 10 for reducing or stopping flow through a tubular structure of a patient, in accordance with various embodiments of the subject technology. Apparatus 10 comprises elongate member 12 arranged to form frame 76 having distal opening 16 and proximal opening 18. Frame 76 is configured to be positioned within a lumen of the tubular structure. Frame 76 includes proximal portion 20, distal portion 24, and middle portion 22 therebetween. Distal portion 24 is tapered such that an outer cross sectional dimension of distal opening 16 is less than an outer cross sectional dimension of middle portion 22. The tapered distal portion 24 may allow for easy passage of a guide wire or a retrieval tool to pass therethrough. Frame 76 is configured to be inverted such that distal portion 24 moves within and toward middle portion 22 for removing frame 76 from within the lumen. Apparatus 10 also comprises flow reducing member 14 coupled to frame 76 such that when frame 76 is positioned within the lumen, flow reducing member 14 substantially reduces or totally obstructs flow of at least one of emboli and fluid flowing through the lumen. In some aspects, flow reducing member 14 may be coupled to frame 76 using surgical suture.

In some embodiments, elongate member 12 is arranged in a spiral configuration to form frame 76. Frame 76 may be beneficially expanded in a radial direction to engage an inner surface of the lumen. Should the inner surface of the lumen apply a radially compressive force on any portion of frame 76, the spiral configuration of frame 76 allows for such a force to be dispersed along the entirety of elongate member 12, thereby providing strong structural support for apparatus 10 to be placed within the lumen. In some embodiments, the spiral configuration of elongate member 12 allows for frame 76 to withstand long-term pulsatile loads of torque and bending, and beneficially reduces risks of fatigue breaks, cracks, etc. In some embodiments, elongate member 12 may be arranged to have more or less coils in the spiral configuration depending on a desired size of frame 76, a desired placement of apparatus 10, a desired compressibility of frame 76, and other suitable factors known to those of ordinary skill in the art. In some embodiments, elongate member 12 is highly flexible while providing sufficient rigidity to be guided through the lumen. In some embodiments, tapered distal portion 24 comprises one to two coils of frame 76.

In some embodiments, frame 76 may be reduced in the radial direction by applying an axial force to a tip of elongate member 12, beneficially allowing for frame 76 to disengage from the inner surface of the lumen and for the repositioning and/or removal of apparatus 10. For example, an axial force in the proximal direction may be applied to a proximal tip of elongate member 12, resulting in the radial reduction of frame 76. Although elongate member 12 is arranged in the spiral configuration, other suitable configurations known to those of ordinary skill in the art may be used. In some embodiments, elongate member 12 comprises one or more anchors configured to engage an inner surface of the lumen for resisting axial movement of frame 76 when frame 76 is deployed within the lumen. For example, the one or more anchors may be protrusions, or hair-like wires of the same material as elongate member 12.

According to certain embodiments, apparatus 10 may be removed from within the lumen by inverting frame 76. For example, an axial force in the proximal direction may be applied to distal portion 24 such that distal portion 24 moves within and toward middle portion 22. In some embodiments, such an inversion causes elongate member 12 to "unwind" from its spiral configuration, in which case the axial force may continue to be applied until elongate member 12 disengages from the inner surface of the lumen. In some embodiments, elongate member 12 may maintain its spiral configuration after the inversion, but otherwise have a reduced cross sectional dimension as an inverted frame 76. In such a case, the inverted frame 76 may be easily removed from within the lumen because of the reduced cross sectional dimension.

According to various embodiments of the subject technology, elongate member 12 may comprises at least one of stainless steel, nickel titanium (NiTi), cobalt chromium (CoCr), titanium, a polymer, a polyester based material, a tyrosine based polycarbonate, a polyethylene based material, Teflon (e.g., including expanded Teflon), and other suitable materials known to those of ordinary skill in the art. In some embodiments, elongate member 12 may comprise at least one of polyethylene, polyglicolide, polylactide, ϵ-caprolactone, polycarbonate, hydroxyalkanote, para dioxinine, PLA, PGA, PLLA, PDLLA, PDO, PCL, and other suitable materials known to those of ordinary skill in the art. In some embodiments, elongate member 12 and/or flow reducing member 14, may comprise a bioabsorbable material, beneficially allowing for their controlled degradation. In some embodiments, elongate member 12 and/or flow reducing member 14 may be formed of bioabsorbable material to have a controlled degradation anywhere between about 3 months to about 3 years depending on the desired application of apparatus 10. In some embodiments, the controlled degradation may be less than about 3 months or greater than about 3 years. For example, hydrolysis of ester linkages or effects of enzymatic degradation may be utilized for the controlled degradation.

In some embodiments, frame 76 may be coated with various suitable agents to allow frame 76 to engage the inner surface of the lumen. For example, frame 76 may be coated with biological glue. In some embodiments, the biological glue may comprise glue from at least one of crab shells, spider webs, gecko feet, burrowing frogs, mussels, and caulobacter crescentus bacteria. In some embodiments, frame 76 may be coated with a friction-resistant coating (e.g., a friction-resistant polymer coating). In some embodiments, radio-opaque markers may be located on frame 75, flow reducing member 14, and/or a catheter delivering apparatus 10 for endovascular or other image-guided procedures. For example, a radio-opaque marker may be placed on a first coil of frame 76. In some embodiments, an outer cross sectional dimension of the first coil is less than an outer cross sectional dimension of a second coil of frame 76, which will allow space for the radio-opaque marker to surround, at least in part, an exterior of the first coil. In some embodiments, the first coil is adjacent to the second coil, and flow reducing member 14 may be coupled to the second coil. In this regard, having the radio-opaque marker placed on the first coil adjacent to the second coil that is coupled to flow reducing member 14 will allow an operator of apparatus 10 to identify where embolization may occur, for example. In some embodiments, the radio-opaque marker may be a platinum iridium alloy or other suitable markers known to those of ordinary skill in the art.

According to various embodiments of the subject technology, flow reducing member 14 may be used to occlude, partially or completely, the tubular structure in which apparatus 10 is deployed. In some embodiments as used herein, occlusion may refer to either partial or complete occlusion. In some embodiments, at least a portion of flow reducing member 14 extends from an exterior of frame 76 into an interior of frame 76 through distal opening 16 to form flap 78 in the interior of frame 76. Flap 78 is configured to substantially prevent distal flow (e.g., from proximal toward distal) through distal opening 16 and facilitate proximal flow (e.g., from distal toward proximal) through distal opening 16. For example, a guide wire may be extended through distal opening 16 for deploying apparatus 10. Flap 78 may be pressed against the guide wire. Upon removing the guide wire in the proximal direction, flap 78 may operate to close distal opening 16 such that distal flow through distal opening 16 is substantially prevented. In some embodiments, flap 78 may serve as a one-way valve to substantially or totally obstruct flow in one direction. For example, flap 78 may substantially or totally obstruct distal flow while allowing proximal flow. Such an arrangement may be beneficially used in partial lung obstruction to treat COPD for example.

In some embodiments, flow reducing member 14 comprises at least one of a polyurethane, a polyanhidrate, expanded polytetrafluoroethylene (ePTFE), and other suitable materials known to those of ordinary skill in the art. In some embodiments, flow reducing member 14 may be elastic. In some embodiments, flow reducing member 14 may be permeable or non-permeable.

According to certain embodiments, a hole may be defined in flow reducing member 14. The hole may allow the guide wire to extend therethrough. In some embodiments, flow reducing member 14 comprises a portion configured to partially, substantially, or totally block the hole when the guide wire is removed therefrom. Swelling material may be disposed in or on the portion, and when fluid contacts the swelling material, the swelling material and the portion may be expanded to substantially or totally block the hole. For example, the portion may comprise a pocket holding the swelling material. In some aspects, the swelling material may be comprised of microparticles. In some aspects, the swelling material may be hydrogel or other suitable swelling material known to those of ordinary skill in the art. When fluid, such as blood, contacts the swelling material, the swelling material and the pocket may expand (e.g., up to 3 to 5 times) to substantially block the hole.

According to certain embodiments, flow reducing member 14 forms a continuous cover without a flap. For example, flow reducing member 14 may form a cover that is disposed over an exterior of distal portion 24, thereby covering distal opening 16. In some embodiments, flow reducing member 14 comprises a self sealing material, which allows for an extension of the guide wire to extend therethrough. Once the guide wire is removed, flow reducing member 14 may be self sealed, allowing for flow reducing member 14 to occlude the tubular structure. In some embodiments, flow reducing member 14 may comprise a plurality of pores each having a diameter of between about 5 microns and about 10 microns, which may be beneficial for occluding blood, for example. In some embodiments, flow reducing member 14 may comprise a plurality of pores each having a diameter less than about 5 microns or greater than about 10 microns. In some embodiments, flow reducing member 14 may comprise a plurality of pores each having a diameter less than about 3 microns. In some embodiments, flow reducing member 14 may comprise a plurality of pores each having a diameter less than about 1 micron. In some embodiments, flow reducing member 14 may comprise a plurality of pores each having a diameter greater than about 13 microns. In some embodiments, flow reducing member 14 may comprise a plurality of pores each having a diameter greater than about 16 microns. Although flow reducing member 14 is shown as disposed over distal portion 24, flow reducing member 14 may be disposed over other portions of frame 76 depending on the desired placement of flow reducing member 14, desired application of apparatus 10, etc. For example, flow reducing member 14 may be disposed over proximal portion 20 or middle portion 22. In another example, flow reducing member 14 may be disposed over proximal portion 20, middle portion 22, and distal portion 24.

In some embodiments, a length of frame 76 may be between about 7 millimeters (mm) and about 9 mm. In some embodiments, the length of frame 76 may be less than about 7 mm or greater than about 9 mm. According to certain embodiments, a combined length of proximal portion 20 and middle portion 22 may be between about 4 mm and about 5 mm to provide adequate anchoring of frame 76 with respect to distal portion 24 (e.g., between about 40% and about 70% of the length of frame 76). In some embodiments, the combined length of proximal portion 20 and middle portion 22 may be less than about 4 mm or greater than about 5 mm. In some embodiments, a length of distal portion 24 may be between about 3 mm and about 4 mm. In some embodiments, the length of distal portion may be less than about 3 mm or greater than about 4 mm. In some embodiments, a diameter of proximal portion 20 and/or middle portion 22 may be between about 2 mm and about 10 mm. In some embodiments, the diameter of proximal portion 20 and/or middle portion 22 may be less than about 2 mm or greater than about 10 mm. In some embodiments, a diameter of distal portion 24 may be between about 0.4 mm and about 0.5 mm. In some embodiments, the diameter of distal portion 24 may be less than about 0.4 mm or greater than about 0.5 mm.

In some embodiments, an average thickness of flow reducing member 14 is between about 0.0005 inches and about 0.006 inches. In some aspects, the average thickness of flow reducing member 14 may be less than about 0.0005 inches or greater than about 0.006 inches. In certain embodiments, an average thickness of a distal portion of flow reducing member 14 is greater than an average thickness of a proximal portion of flow reducing member 14. Such a configuration may ensure that more flow may be reduced at the distal portion of flow reducing member 14, for example near distal opening 16. In some embodiments, the average thickness of the distal portion of flow reducing member 14 is between about 0.002 inches and about 0.012 inches. In some embodiments, the average thickness of the distal portion of flow reducing member 14 may be less than about 0.002 inches or greater than about 0.012 inches. In some embodiments, the average thickness of the proximal portion of flow reducing member 14 is between about 0.0005 inches and about 0.006 inches. In some embodiments, the average thickness of the proximal portion of flow reducing member 14 may be less than about 0.0005 inches or greater than about 0.006 inches.

According to various aspects of the subject technology, apparatus 10 may be used for various applications for reducing or stopping flow through a tubular structure of a patient. Apparatus 10 may be used for rapid, well-controlled, and reliable occlusion of tubular structures. For example, the tubular structure may comprise at least one of a blood vessel, a Fallopian tube, a cervical canal, a vagina, a cervix, a vas deferens, a bronchus, a ureter, a colon, a rectum, an anus, a bio duct, a pancreatic duct, or other suitable tubular structures known to those of ordinary skill in the art. In some embodiments, apparatus 10 may be used for temporary occlusion in cases of lung disease, or for temporary occlusion of female reproductive organs for contraceptive purposes. In some embodiments, apparatus 10 may be removed, or flow may be restored through the tubular structure to restore original organ functions.

In some embodiments, apparatus 10 may be used for various endoluminal occlusion procedures, including procedures for the lungs (e.g., selective endobronchial occlusion for lung reduction, occlusion of bronchopleural or bronchocutaneous fistulas, endovascular occlusion of pulmonary AVMs and fistulas or aortopulmonary anastomoses) and procedures for reproductive organs (e.g., endoluminal occlusion of vas deferens or Fallopian tubes for minimally-invasive contraceptive intervention, endovascular occlusion of varicocele in males and low abdominal gonadal veins for reducing or completely eliminating chronic pelvic pain syndrome in females). In some embodiments, apparatus 10 may be used for stopping blood loss from a damaged blood vessel, closing an abnormal blood vessel or a blood vessel supplying a vascular anomaly, or interrupting blood supply to an organ or part of an organ for permanent devascularization (e.g., closure of splenic artery in spleen laceration, devascularization of tissues involved by neoplastic process, either pre-operatively or as a palliative measure). In some embodiments, apparatus 10 may be used for various endovascular (e.g., neural and peripheral) procedures including procedures for giant cerebral and skull base aneurysms (ruptured and non-ruptured), head and neck arteriovenous fistulas, dissecting intracranial and extracranial vessels, traumatic and non-traumatic vessel injury or rupture (e.g., pelvic hemorrhages in trauma patients, carotid blow-out in patients with head and neck cancers, hemorrhage induced by a neoplasia, etc.), and devascularization prior to (or as an alternative to) surgical resection of various organs or tumors.

In certain embodiments, apparatus 10 may be used for various organs, including for example, the spleen (e.g., endovascular occlusion as a preoperative intervention or as an alternative to surgical resection with indications including traumatic hemorrhage, hypersplenism, bleeding secondary to portal hypertension or splenic vein thrombosis, and various disorders such as thalassemia major, thrombocytopenia, idiopathic thrombocytopenic purpura, Gaucher disease, and Hodgkin disease), the liver (e.g., occlusion of portal veins collaterals as adjunct to a transjugular intrahepatic portosystemic shunt (TIPS), occlusion of the TIPS itself in cases of encephalopathy, occlusion of intrahepatic arterioportal fistulas), the kidney (e.g., endoluminal uretheral occlusion for intractable lower urinary tract fistula with urine leakage, or for the treatment of urethra-arterial fistulae, endovascular occlusion as an alternative to surgical resection for end-stage renal disease or renovascular hypertension requiring unilateral or bilateral nephrectomy and renal transplant with native kidneys in situ), and the heart (e.g., occlusion of coronary arteriovenous fistulas, transarterial embolization of Blalock-Taussig shunts). The application of apparatus 10 is not limited to applications for human patients, but may also include veterinary applications.

In some embodiments, apparatus 10 comprises a tube configured to extend through flow reducing member 14 and distal opening 16 to be positioned at a target site of the patient. Apparatus 10 also comprises a vacuum source configured to apply a vacuum through the tube for removing at least one of emboli and fluid from the target site. For example, the tube may be placed in a diseased area that has been subjected to occlusion, and the tube may be used to remove body fluids and/or solid components (e.g., blood clots) from the diseased area.

Figure 2:
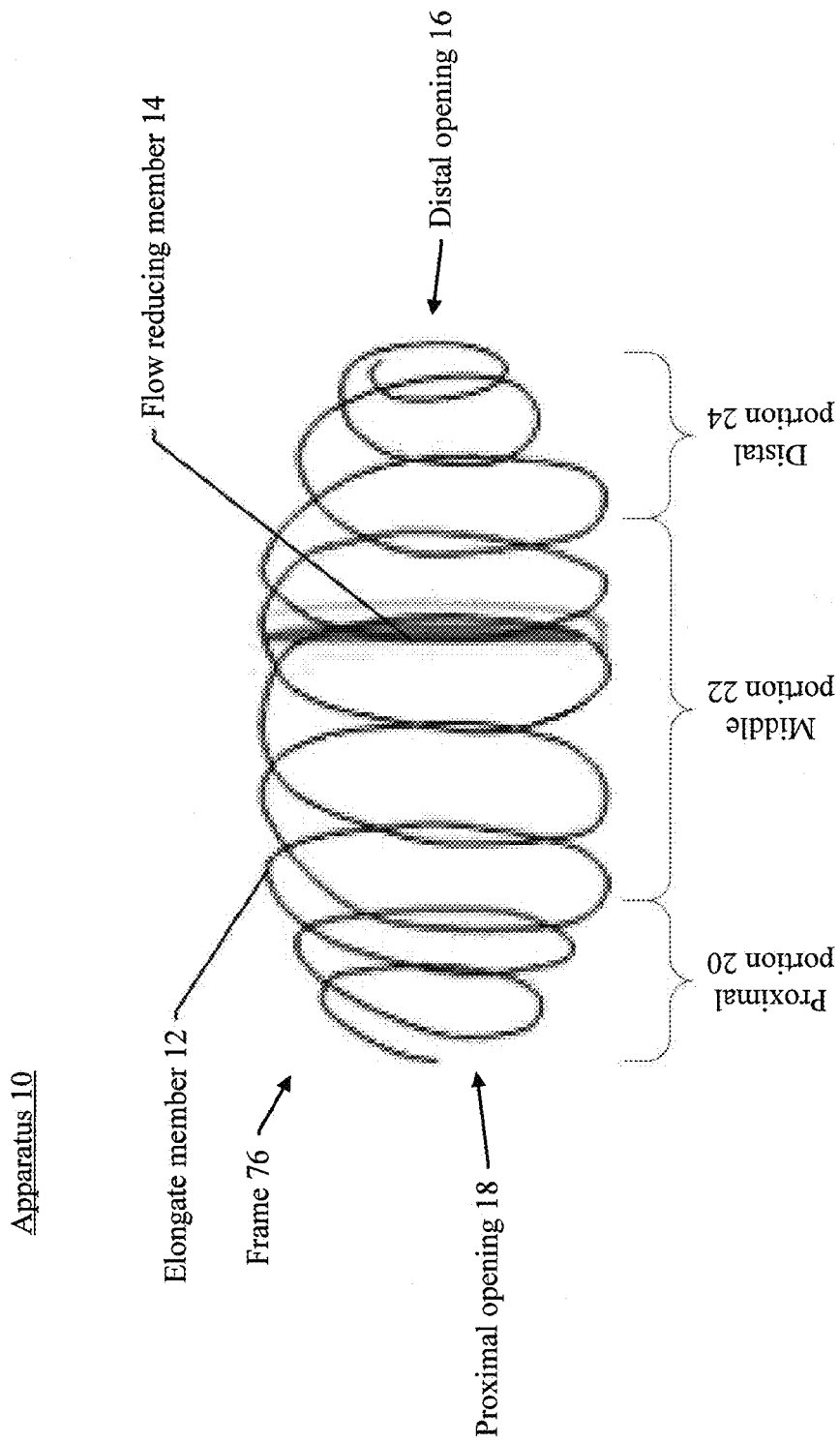
FIG. 2 illustrates an example of an apparatus, in accordance with various embodiments of the subject technology.

FIG. 2 illustrates an example of apparatus 10, in accordance with various embodiments of the subject technology. In some embodiments, proximal portion 20 is tapered such that an outer cross sectional dimension of proximal opening 18 is less than the outer cross sectional dimension of middle portion 22. The tapering of proximal portion 20 provides several advantages. For example, apparatus 10 may be deployed within a lumen of a tubular structure of a patient. Removing or repositioning apparatus 10 within the lumen may cause apparatus 10 to shift axially along the lumen. In removing apparatus 10 from within the lumen, a catheter may be placed proximal to apparatus 10 to receive apparatus 10. When apparatus 10 is being removed, such as by inversion as described above, apparatus 10 may shift proximally. Thus, the tapering of proximal portion 20 may ensure that apparatus 10 shifts into the catheter when apparatus 10 is being removed.

Furthermore, when flow reducing member 14 is used to occlude the tubular structure, flow reducing member 14 may capture emboli or other particles flowing through the lumen of the tubular structure. In some embodiments, the emboli or other particles may be contained or trapped within an interior of frame 76 because of the tapered portions of both proximal portion 20 and distal portion 24. For example, flow reducing member 14 may be used to reduce or stop blood flow in a vessel. Blood may clot as a result of the reduction or stoppage of flow by flow reducing member 14. In some embodiments, the blood clot may be trapped within the interior of frame 76 between the tapered proximal portion 20 and flow reducing member 14. In some embodiments, the tapered proximal portion 20 may substantially prevent the blood clot from flowing proximally out of the interior of frame 76.

According to various embodiments of the subject technology, flow reducing member 14 may be disposed in an interior of frame 76. As shown in FIG. 2, flow reducing member 14 is disposed in the interior of frame 76 and is also coupled to middle portion 22. Such a configuration may beneficially allow for flow reducing member 14 to occlude the tubular structure when apparatus 10 is disposed within the lumen of the tubular structure. Because middle portion 22 comprises portions of frame 76 that expand and engage the inner surface of the lumen, flow reducing member 14—by being coupled to middle portion 22—may be stretched great enough to occlude the tubular structure.

According to certain embodiments, the outer cross sectional dimension of proximal opening 18 may be larger than an outer cross sectional dimension of distal opening 16, which may be useful for achieving a reduction or stoppage of flow through distal opening 16.

Figure 3:
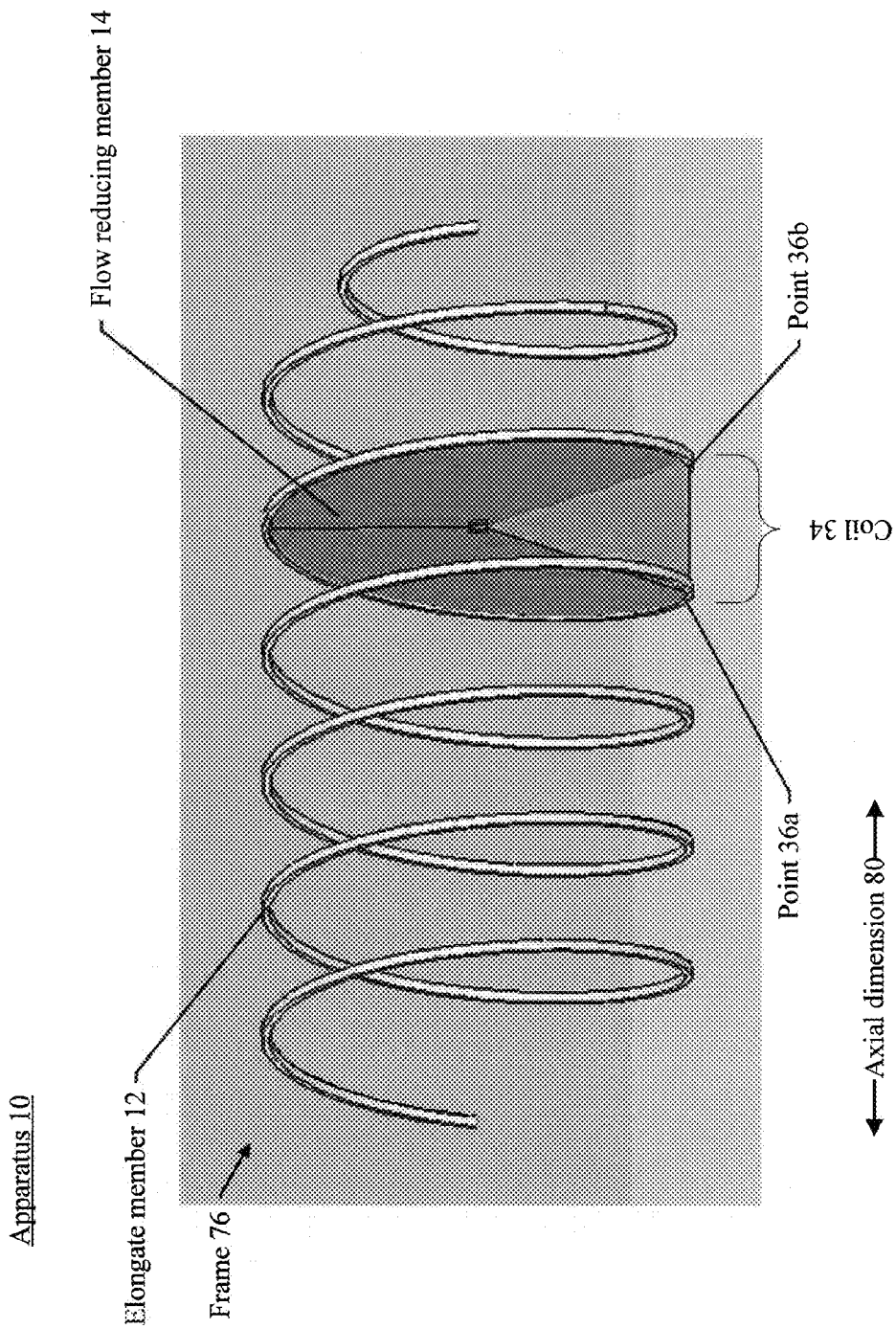
FIG. 3 illustrates an example of an apparatus having a flow reducing member disposed in an interior of a frame, in accordance with various embodiments of the subject technology.

FIG. 3 illustrates an example of apparatus 10 having flow reducing member 14 disposed in an interior of frame 76, in accordance with various embodiments of the subject technology. Flow reducing member 14 may be coupled to coil 34 of frame 76 such that flow reducing member 14 substantially covers an opening through coil 34. For example, a portion of elongate member 12 from point 36a on elongate member 12 to point 36b on elongate member 12 forms coil 34. In some embodiments, flow reducing member 14 is coupled to elongate member 12 from point 36a to point 36b on elongate member 12. In some embodiments, if flow reducing member 14 is coupled to one coil of frame 76, an opening through the coil may be occluded. In some embodiments, flow reducing member 14 may be coupled to more than one coil of frame 76.

In certain embodiments, a thickness of coil 34 measured along axial dimension 80 of first frame 76 is less than a thickness of another coil of frame 76 measured along axial dimension 80. Having a low thickness may beneficially allow flow reducing member 14 to cover the opening through coil 34 without being stretched too far along axial dimension 80.

Figure 4:
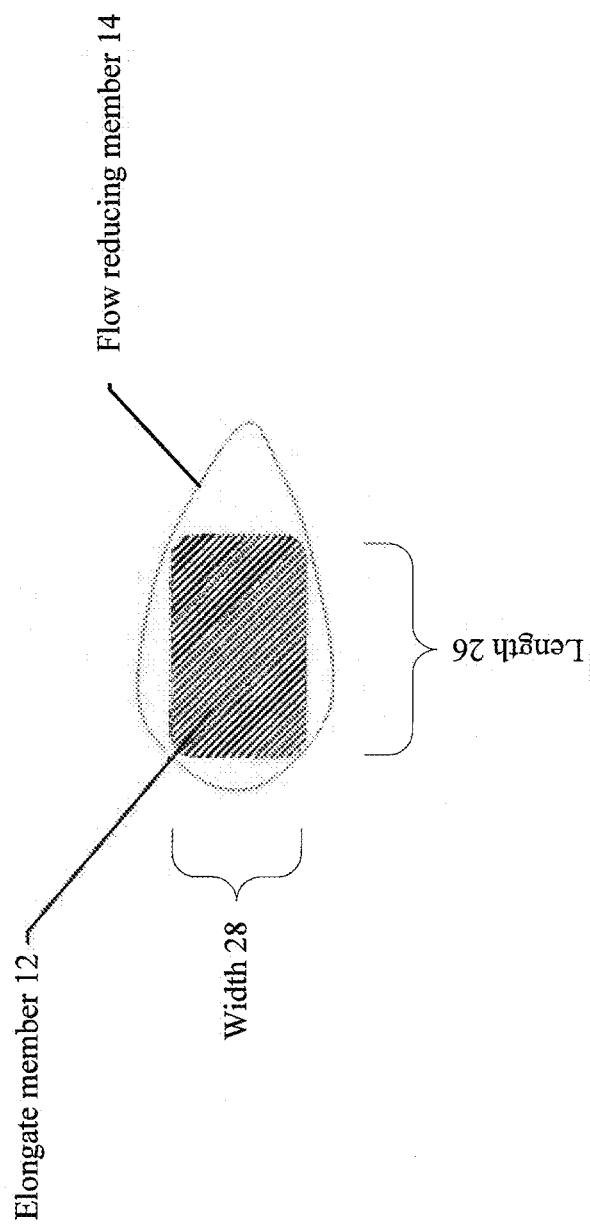
FIG. 4 illustrates a cross sectional dimension of an elongate member, in accordance with various embodiments of the subject technology.

FIG. 4 illustrates a cross sectional dimension of elongate member 12, in accordance with various embodiments of the subject technology. In some embodiments, elongate member 12 comprises a substantially rectangular cross section. It was found that such a cross section beneficially allowed for apparatus 10 to stabilize within a lumen of a tubular structure, thereby minimizing the axial shifting of apparatus 10 when deployed within the lumen. Furthermore, the substantially rectangular cross section of elongate member 12 provided additional strength for preventing frame 76 from collapsing under the force exerted onto frame 76 by the lumen. In some embodiments, the substantially rectangular cross section allows elongate member 12 to be easily arranged into a spiral configuration to form frame 76.

In some embodiments, the corners of the rectangular cross section are curved. In some embodiments length 26 of the rectangular cross section is between about 0.008 inches and about 0.014 inches. In some embodiments, length 26 may be less than about 0.008 inches or greater than about 0.014 inches. In some embodiments, width 28 of the rectangular cross section is between about 0.004 inches and about 0.006 inches. In some embodiments, width 28 may be less than about 0.004 inches or greater than about 0.006 inches.

According to certain embodiments, flow reducing member 14 may be coupled to elongate member 12 as shown in FIG. 4. For example, flow reducing member 14 may wrap around elongate member 12 from one point along elongate member 12 to another point along elongate member 12 to form a drum-like cover through an opening of a coil of frame 76, for example as shown in FIG. 3.

Figure 5A:
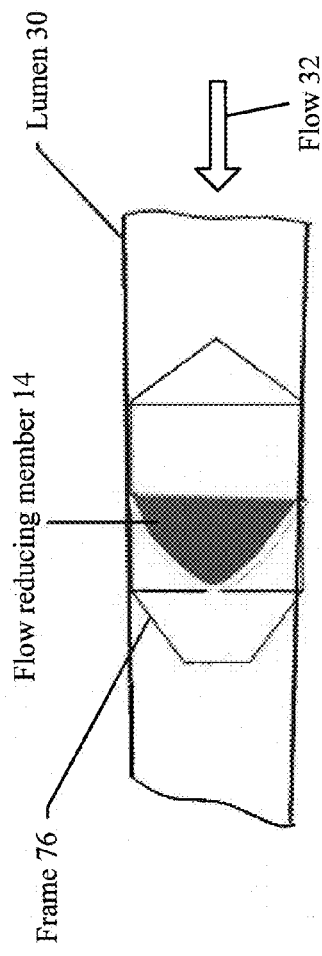
FIGS. 5A and 5B illustrate an apparatus deployed within a lumen of a tubular structure of a patient, in accordance with various embodiments of the subject technology.
Figure 5B:
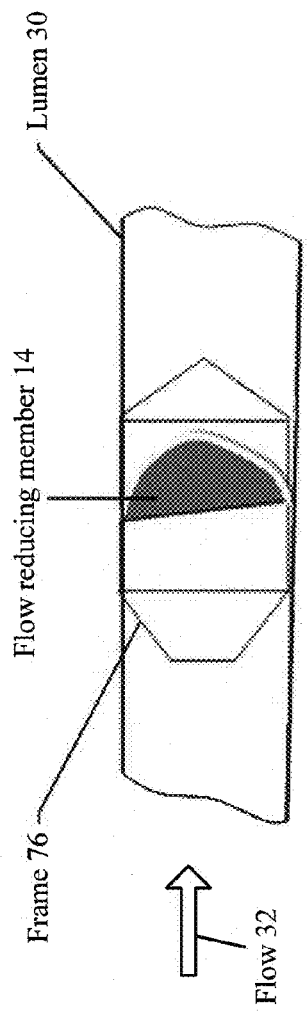

FIGS. 5A and 5B illustrate apparatus 10 deployed within lumen 30 of a tubular structure of a patient, in accordance with various embodiments of the subject technology. For simplicity, frame 76 is illustrated as an outline. As shown in these figures, flow reducing member 14 is coupled to middle portion 22 in an interior of frame 76. One benefit of having flow reducing member 14 coupled to middle portion 22 in the interior of frame 76 is that flow reducing member 14 may be given enough space to stretch in either direction depending on flow 32. For example, as shown in FIG. 5A, flow 32 is in the proximal direction, and hence, flow reducing member 14 may also be stretched in the proximal direction. As shown in FIG. 5B, flow 32 is in the distal direction, and hence, flow reducing member 14 may be stretched in the distal direction. By coupling flow reducing member 14 to middle portion 22 in the interior of frame 76, flow reducing member 14 may be used to reduce or stop flow 32 through lumen 30 in either direction.

Figure 6:
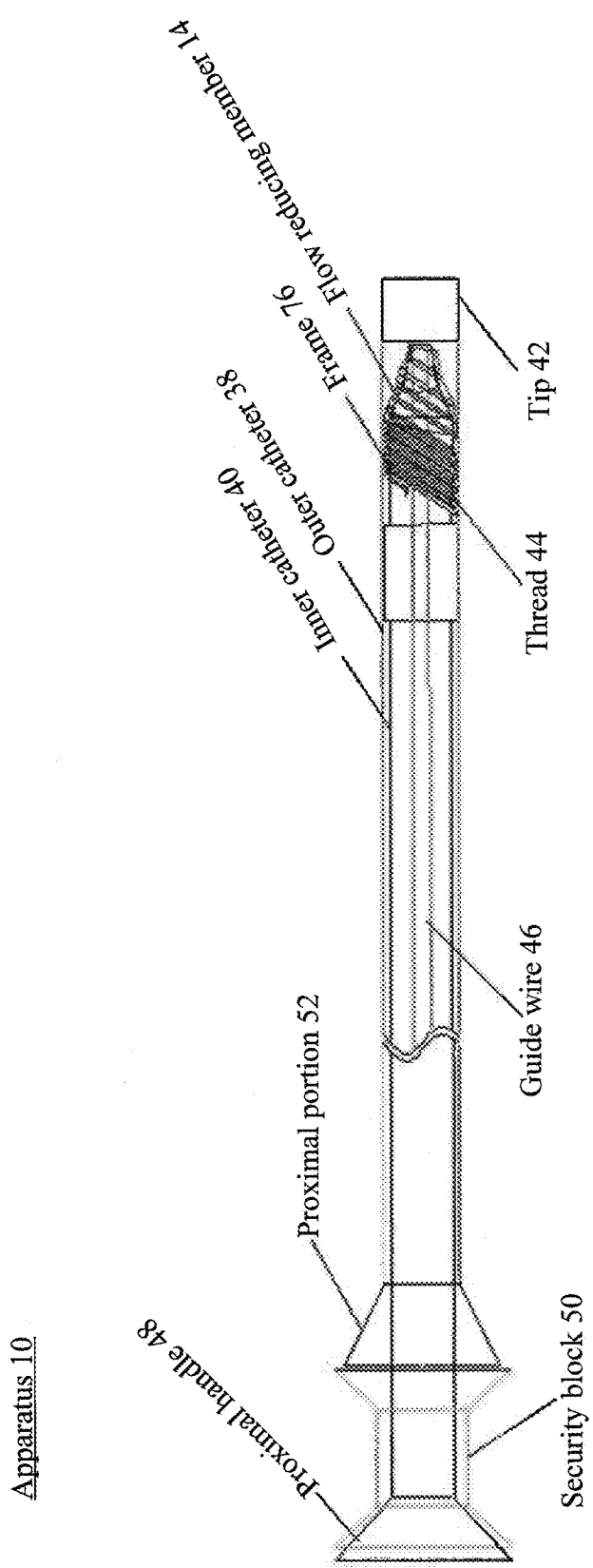
FIG. 6 illustrates an example of a frame and a flow reducing member being positioned within an outer catheter, in accordance with various embodiments of the subject technology.

FIG. 6 illustrates an example of frame 76 and flow reducing member 14 being positioned within outer catheter 38, in accordance with various embodiments of the subject technology. In some aspects, "catheter" as used herein may be given at least its ordinary meaning. In some aspects, "catheter" as used herein may refer to any elongate member having a lumen passing therethrough. A catheter, therefore, can be tubular or have other suitable cross sectional shapes, such as at least one of elliptical and polygonal (e.g., triangular, rectangular, hexagonal, octagonal, etc.) cross sectional shapes. Apparatus 10 may comprise outer catheter 38 configured to be positioned within a lumen at a first deployment site. Apparatus 10 may also comprise inner catheter 40 disposed within outer catheter 38. Frame 76 is configured to be positioned between inner catheter 40 and outer catheter 38 for stowage of frame 76 before frame 76 is deployed within the lumen. As shown in FIG. 6, flow reducing member 14 is disposed over distal portion 24 of frame 76. In some embodiments, tip 42 may be a soft tip useful for reducing trauma and/or friction when outer catheter 38 is being navigated through the lumen and being positioned at the first deployment site.

In some embodiments, inner catheter 40 comprises proximal handle 48. Frame 76 and flow reducing member 14 may be deployed from outer catheter 38 by shifting proximal handle 48 and inner catheter 40 distally relative to outer catheter 38 until frame 76 and flow reducing member 14 extend beyond a distal opening of outer catheter 38 into the lumen. In some embodiments, apparatus 10 further comprises security block 50 coupled to proximal handle 48. Security block 50 may be configured to substantially prevent proximal handle 48 and inner catheter 40 from shifting distally relative to outer catheter 38 by acting a stop to prevent proximal handle 48 from contacting proximal portion 52 of outer catheter 38. In some embodiments, security block 50 may be designed to have a predetermined length corresponding to a distance needed to shift proximal handle 48 and inner catheter 40 distally relative to outer catheter 38 to fully deploy frame 76 and flow reducing member 14 from outer catheter 38. For example, if proximal handle 48 is shifted distally relative to outer catheter 38 such that proximal handle 48 contacts proximal portion 52 of outer catheter 38, an operator of apparatus 10 may understand that frame 76 and flow reducing member 14 has been fully deployed from outer catheter 38.

Figure 7A:
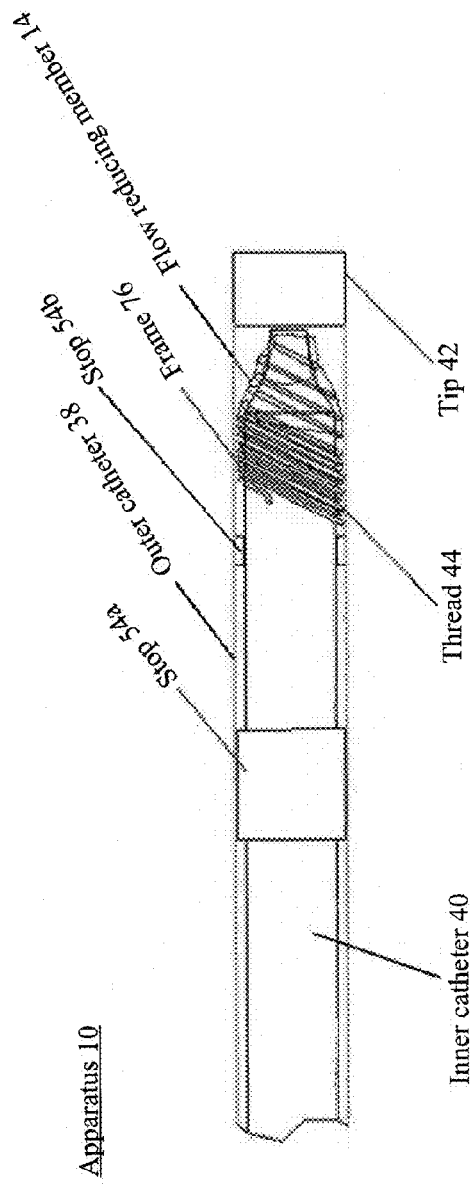
FIGS. 7A and 7B illustrate detailed views of a frame and a flow reducing member positioned within an outer catheter, in accordance with various embodiments of the subject technology.
Figure 7B:
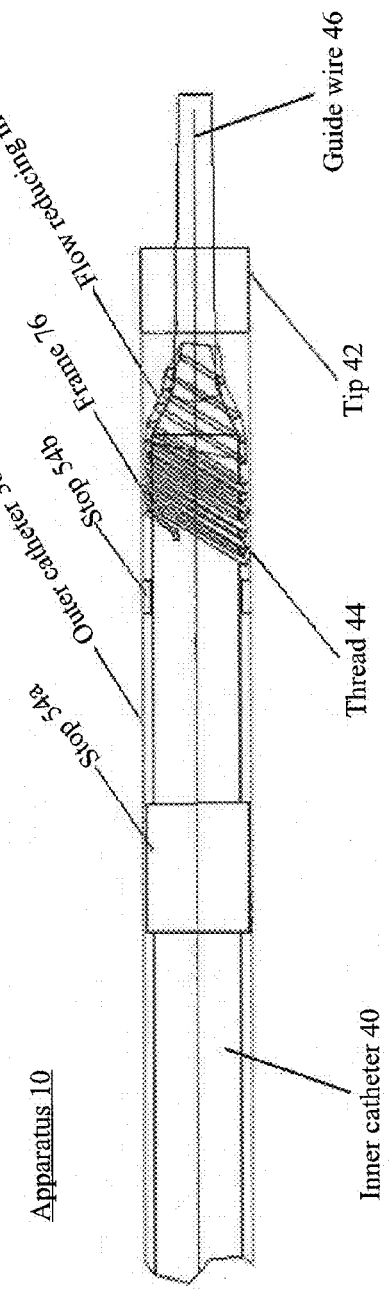

FIGS. 7A and 7B illustrate detailed views of frame 76 and flow reducing member 14 positioned within outer catheter 38, in accordance with various embodiments of the subject technology. In some embodiments, apparatus 10 comprises one or more threads 44 formed in or on an outer surface of inner catheter 40 such that elongate member 12 wraps around the one or more threads 44 for securing elongate member 12 to inner catheter 40. The one or more threads 44 may be made of nylon, metal, or other suitable material known to those of ordinary skill in the art. In some embodiments, the one or more threads 44 may be made of metal for precise placement of elongate member 12 between the one or more threads 44. In some embodiments, flow reducing member 14 may be of a suitable thickness to be positioned between the outer surface of inner catheter 40 and an inner surface of outer catheter 38. For example, an average thickness of flow reducing member 14 may be between about 0.0005 inches and about 0.006 inches, or other suitable ranges.

In some embodiments, outer catheter 38 may prevent frame 76 from radially expanding such that frame 76 is secured between the inner surface of outer catheter 38 and the outer surface of inner catheter 40. In some embodiments, when inner catheter 40 is shifted distally relative to outer catheter 40 until frame 76 extends beyond a distal opening of outer catheter 40 into the deployment site, outer catheter 38 no longer prevents frame 76 from radially expanding. In this regard, frame 76 may expand from an undeployed configuration into a deployed configuration such that frame 76 engages an inner surface of the lumen. In some embodiments, frame 76 does not automatically expand into a deployed configuration, but is expanded into the deployed configuration with a balloon. In some embodiments, frame 76 may be self expandable.

According to various embodiments of the subject technology, frame 76 and flow reducing member 14 may be accurately deployed and/or repositioned at a deployment site. For example, if an operator of apparatus 10 decides that an initial placement of frame 76 and flow reducing member 14 is undesirable, the operator may redeploy and/or reposition the frame 76 and flow reducing member 14 to another deployment site. In some embodiments, inner catheter 40 is configured to shift distally relative to outer catheter 38 until a portion of frame 76 extends beyond a distal opening of outer catheter 38 into a first deployment site for partially deploying frame 76 from outer catheter 38. Inner catheter 40 is configured to shift proximally relative to outer catheter 38 until the portion of frame 76 is retracted proximally into outer catheter 38 for retracting frame 76 into outer catheter 38. In some embodiments, because a proximal portion of elongate member 12 is still secured to the one or more threads 44, frame 76 is also retracted once inner catheter 40 is retracted. Outer catheter 38 is configured to be positioned within the lumen at a second deployment site for deploying frame 76 at the second deployment site. Inner catheter 40 is configured to shift distally relative to outer catheter 38 until frame 76 extends beyond the distal opening of outer catheter 38 into the second deployment site for deploying frame 76 from outer catheter 38 into the second deployment site.

In some embodiments, apparatus 10 further comprises one or more stops (e.g., stops 54*a* and 54*b*) disposed between outer catheter 38 and inner catheter 40. In some embodiments, stop 54*b* is coupled to an inner surface of outer catheter 38 and is disposed proximal frame 76 when frame 76 is positioned between inner catheter 40 and outer catheter 38. Stop 54a is coupled to an outer surface of inner catheter 40 and is disposed proximal stop 54b. In some embodiments, when inner catheter 40 is shifted distally relative to outer catheter 38 for deploying frame 76, stop 54a engages stop 54b to substantially prevent inner catheter 40 from further distal shifting relative to the outer catheter.

In some embodiments, stop 54b may be coupled to either the inner surface of outer catheter 38 or the outer surface of inner catheter, and may be configured to substantially prevent frame 76 from moving proximally relative to at least one of outer catheter 38 and inner catheter 40. As shown in FIG. 6B, apparatus 10 may further comprise guide wire 46 configured to extend through inner catheter 40 and distal opening 16 of frame 76.

Figure 8:
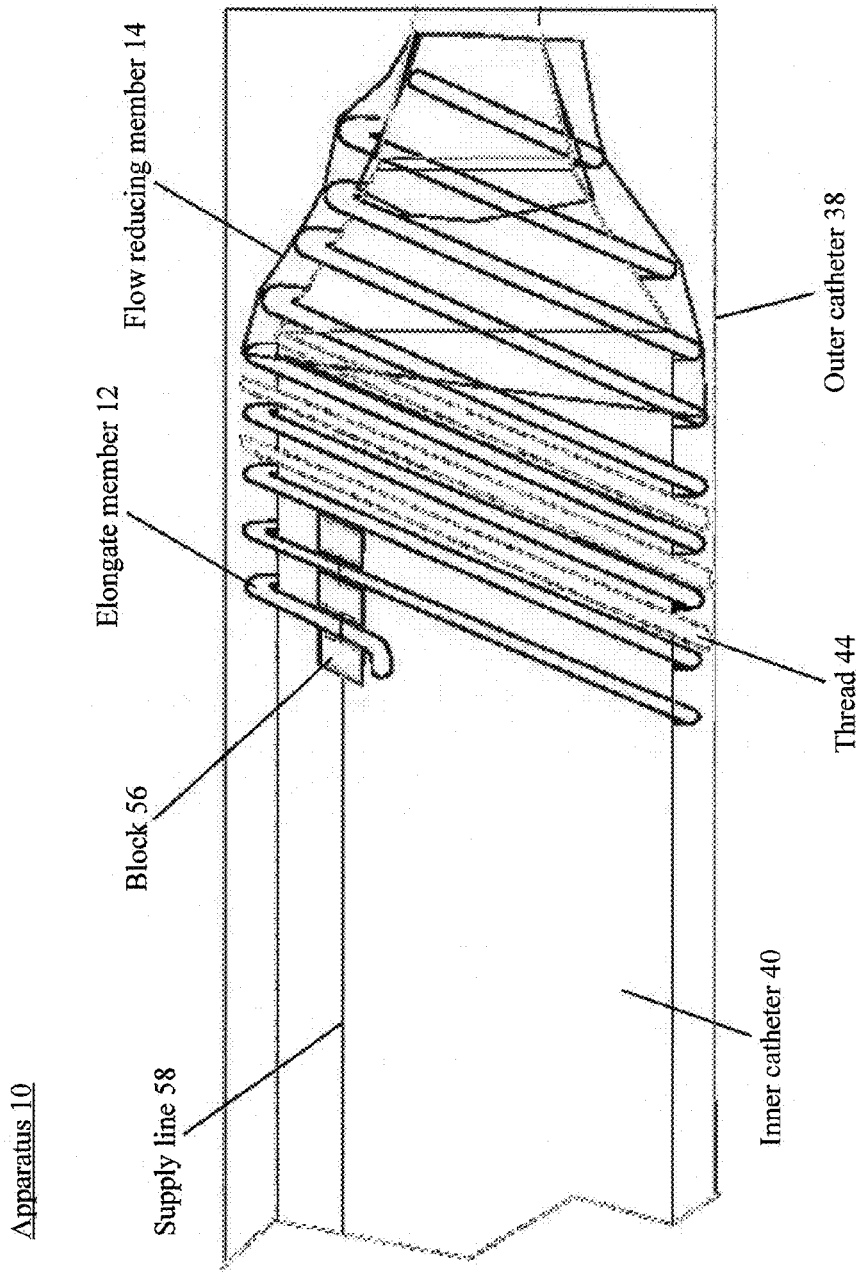
FIG. 8 illustrates an example of a frame and a flow reducing member positioned within an outer catheter, in accordance with various embodiments of the subject technology.

FIG. 8 illustrates an example of frame 76 and flow reducing member 14 positioned within outer catheter 38, in accordance with various embodiments of the subject technology. In some embodiments, apparatus 10 may comprise one or more blocks 56 disposed on an outer surface of inner catheter 40 such that elongate member 12 wraps around the one or more blocks 56 for securing elongate member 12 to inner catheter 40. In some embodiments, the one or more blocks 56 comprise electroactive polymer (EAP) and are configured to swell when electric signals are applied to the one or more blocks 56. Elongate member 12 wrapped around the one or more blocks 56 may be substantially locked to the one or more blocks 56 when the electric signals are applied. For example, in deploying frame 76 and flow reducing member 14, the electric signals may not be applied to allow frame 76 to disengage from inner catheter 40 and the one or more blocks 56. However, should repositioning be desired, the electric signals may be applied to secure a proximal portion of elongate member 12 to inner catheter 40, and inner catheter 40 may subsequently be retracted proximally to also retract frame 76 into outer catheter 38 for repositioning outer catheter 38 at another deployment site.

Figure 9:
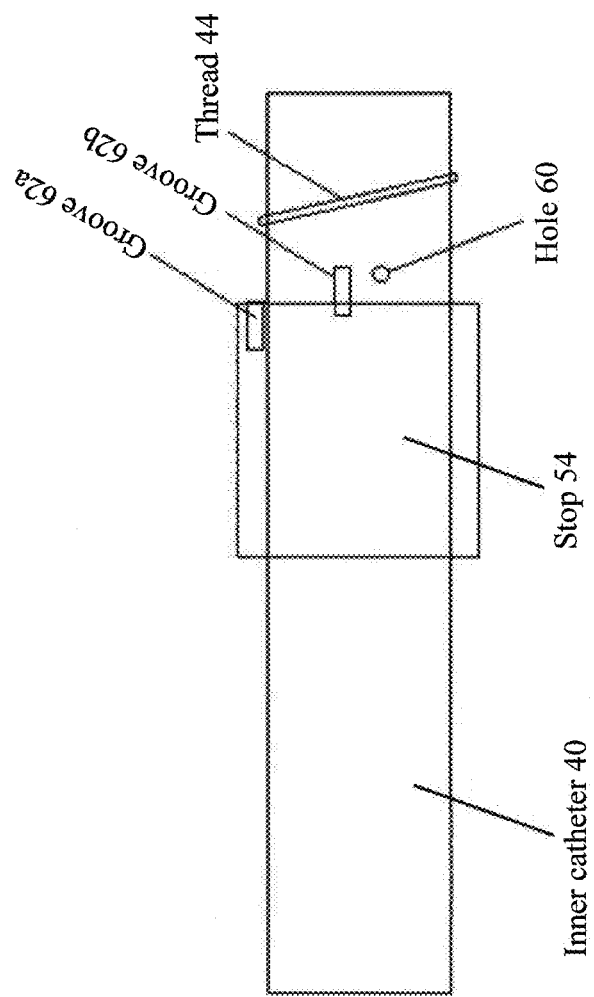
FIG. 9 illustrates an example of an inner catheter, in accordance with various embodiments of the subject technology.

FIG. 9 illustrates an example of inner catheter 40, in accordance with various embodiments of the subject technology. In some embodiments, inner catheter 40 comprises hole 60 configured such that a proximal tip of elongate member 12 extends through hole 60 from an exterior of inner catheter 40 into an interior of inner catheter 40 for securing frame 76 to inner catheter 40. In some embodiments, inner catheter comprises one or more grooves (e.g., groove 62a and 62b) configured such that the proximal tip of elongate member 12 is disposed in the one or more grooves for securing frame 76 to inner catheter 40. For example, groove 62a may be formed on stop 54. Groove 62b may be formed on an outer surface of inner catheter 40.

FIGS. 10A and 10B illustrate an example of frame 76 and flow reducing member 14 positioned within outer catheter 38, in accordance with various embodiments of the subject technology. In some embodiments, flow reducing member 14 may be coupled to middle portion 22 of frame 76 in an interior of frame 76, as shown in FIG. 10A. Thus, when frame 76 and flow reducing member 14 are stowed within outer catheter 38, inner catheter 40 may push flow reducing member 14 towards an interior of distal portion 24 of frame 76. In some embodiments, flow reducing member 14 may be disposed over distal portion 24 of frame 76, as shown in FIG. 10B. According to various embodiments of the subject technology, distal portion 24 and flow reducing member 14 may extend distally beyond distal opening 64 of outer catheter 38 such that when outer catheter 38 is moved within the lumen to a deployment site, the distally extended portion of flow reducing member 14, shown in either FIG. 10A or 10B, is configured to engage a wall of the lumen to reduce friction and potential vessel injury during device tracking and delivery to the deployment site. Thus, the distally extended portion of flow reducing member 14 may act as a soft tip when outer catheter 38 is being navigated through the lumen and/or positioned within the lumen. In such a case, tip 42 (e.g., as shown in FIG. 6) may not be necessary. In some embodiments, the distally extended portion of flow reducing member 14 may be extended about 2 mm beyond distal opening 64. In some embodiments, the distally extended portion of flow reducing member 14 may be extended less than about 2 or greater than about 2 mm beyond distal opening 64.

Figure 11:
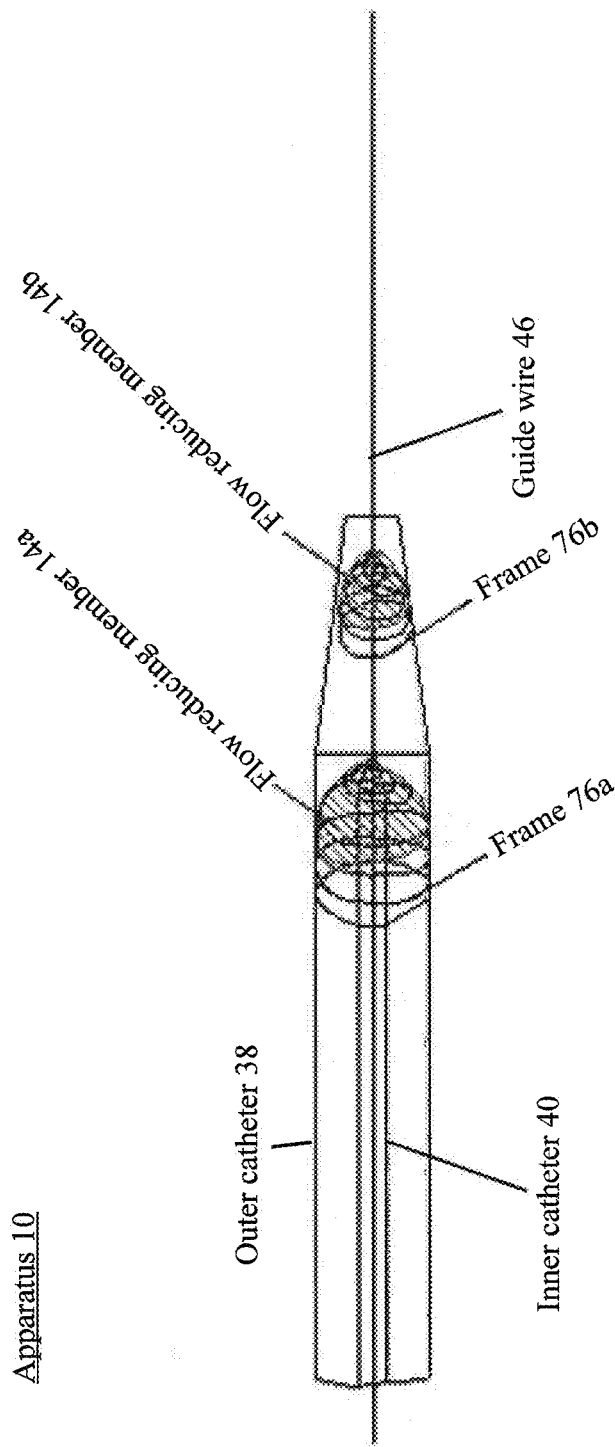
FIG. 11 illustrates an example of two frames and two flow reducing members positioned within an outer catheter, in accordance with various embodiments of the subject technology.

FIG. 11 illustrates an example of two frames 76 (e.g., frames 76a and 76b) and two flow reducing members 14 (e.g., flow reducing members 14a and 14b) positioned within outer catheter 38, in accordance with various embodiments of the subject technology. In some embodiments, apparatus 10 may comprise a second frame and flow reducing member pair (e.g., frame 76b and flow reducing member 14b) to be implanted within a lumen together with a first frame and flow reducing member pair (e.g., frame 76a and flow reducing member 14a). Having a pair of frames 76 and flow reducing members 14 deployed from the same outer catheter 38 may simplify surgery techniques to implant these devices. In some embodiments, time and effort may be saved by deploying the pair of frames 76 and flow reducing member 14 from the same outer catheter 38.

In some embodiments, frame 76b is configured to be positioned between outer catheter 38 and guide wire 46 for stowage of frame 76b before frame 76b is deployed within the lumen. Frame 76b may be deployed in a manner similar to the deployment of frame 76a as described above. For example, one or more threads may be formed in or on an outer surface of guide wire 46 such that the elongate member of frame 76b wraps around the one or more threads for securing the elongate member of frame 76b to guide wire 46. In some embodiments, the elongate member of frame 76b may wrap around guide wire 46 with or without threads.

In some embodiments, one or more blocks may be disposed on an outer surface of guide wire 46 such that the elongate member of frame 76b wraps around the one or more blocks for securing the elongate member of frame 76b to guide wire 46. In some embodiments, the one or more blocks may comprise electroactive polymer (EAP) and are configured to swell when electric signals are applied to the one or more blocks. The elongate member of frame 76b wrapped around the one or more blocks may be substantially locked to the one or more blocks when the electric signals are applied.

In certain embodiments, flow reducing members 14a and 14b may be disposed over various portions of frames 76a and 76b, respectively, depending on their desired applications. For example, flow reducing member 14a is disposed over a distal portion of frame 76a while flow reducing member 14b is disposed over a distal portion of frame 76b. In some embodiments, flow reducing member 14a is disposed over the distal portion of frame 76a while flow reducing member 14b is disposed over a proximal portion of frame 76b.

Figure 12:
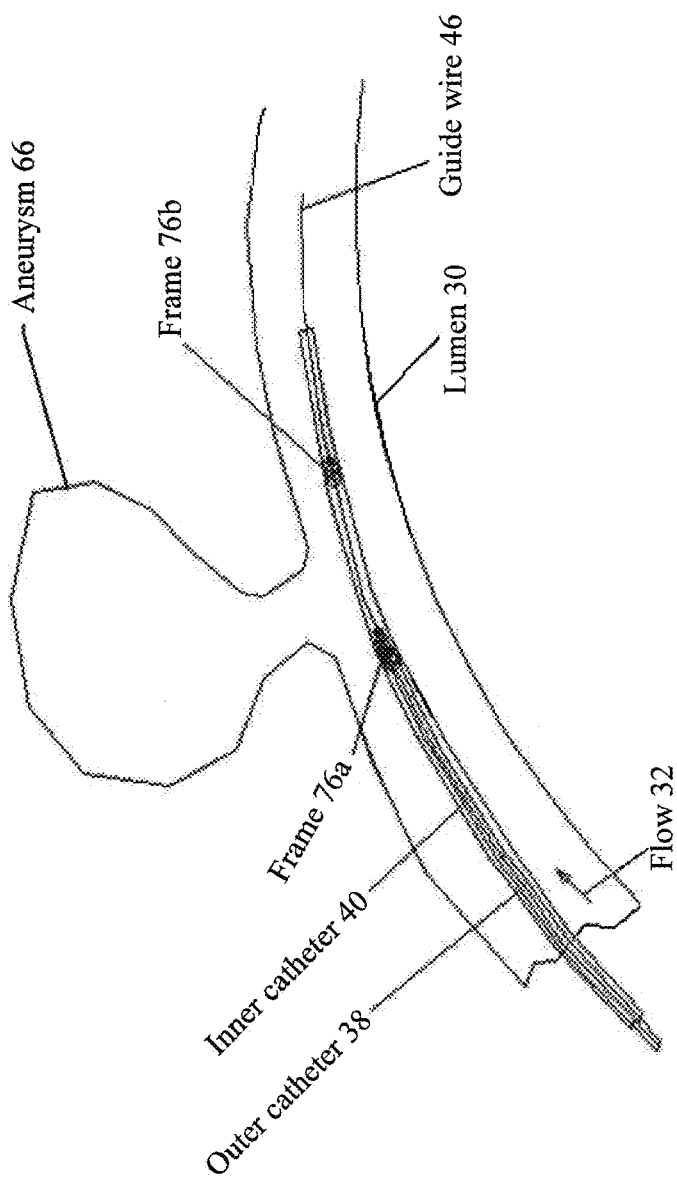
FIG. 12 illustrates an example of deploying frames, along with corresponding flow reducing members, in accordance with various embodiments of the subject technology.

FIG. 12 illustrates an example of deploying frames 76, along with corresponding flow reducing members 14, in accordance with various embodiments of the subject technology. Outer catheter 38 may be positioned within lumen 30 at a first deployment site to deploy frame 76b. For example, the first deployment site may be to the right of aneurysm 66, as shown in FIG. 12. Guide wire 46 is configured to shift distally relative to outer catheter 38 until frame 76b extends beyond a distal opening of outer catheter 38 into the first deployment site for deploying frame 76b from outer catheter 38. In some embodiments, frame 76b may also partially deployed, retracted, and repositioned in a manner similar to frame 76a described above for repositioning frame 76b at a different deployment site. After deployment of frame 76b, outer catheter 38 may then be positioned within lumen 30 at a second deployment site for deploying frame 76a at the second deployment site. For example, the second deployment site may be to the left of aneurysm 66, as shown in FIG. 12. Inner catheter 40 is configured to shift distally relative to outer catheter 38 until frame 76a extends beyond the distal opening of outer catheter 38 into the second deployment site.

Figure 13:
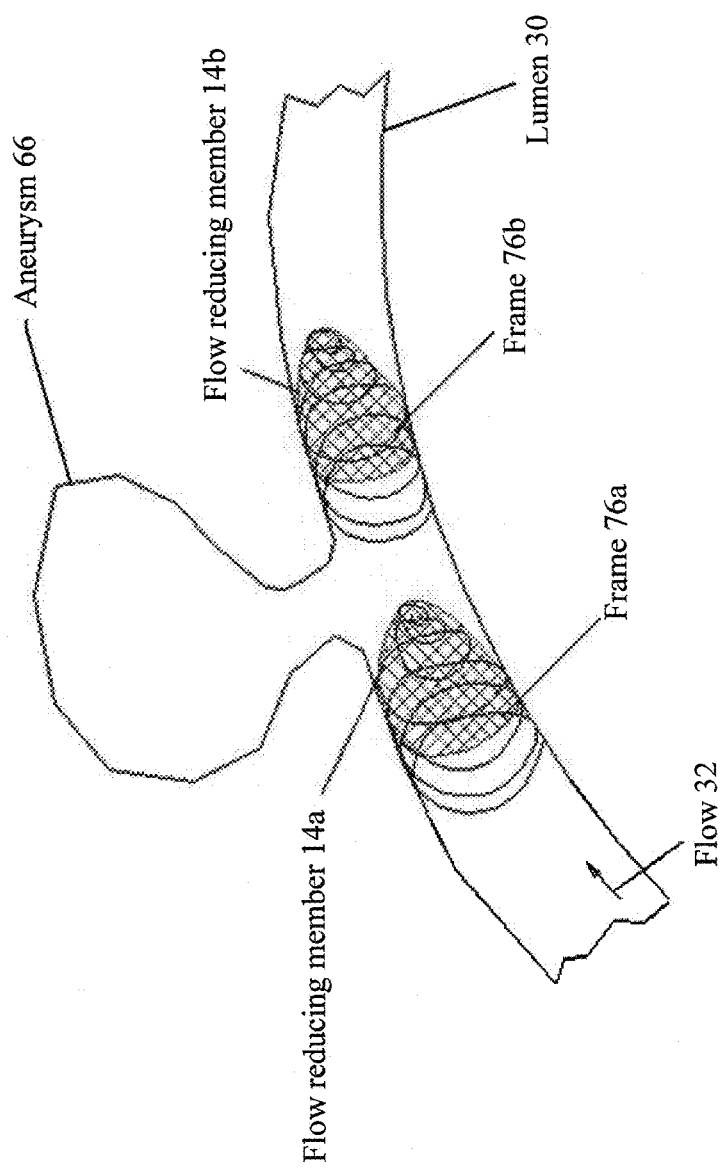
FIG. 13 illustrates an example of frames, along with corresponding flow reduction members, deployed within a lumen for occluding an aneurysm, in accordance with various embodiments of the subject technology.

FIG. 13 illustrates an example of frames 76, along with corresponding flow reduction members 14, deployed within lumen 30 for occluding aneurysm 66, in accordance with various embodiments of the subject technology. In some embodiments, frame 76b and flow reducing member 14b may be placed behind frame 76a and flow reducing member 14a, relative to flow 32, in order to reduce or stop flow that may travel from a direction opposite to flow 32. Frame 76b and flow reducing member 14b may also used to reduce or stop flow that may travel from within aneurysm 66, which may include blood clots. In some embodiments, flow reducing members 14 may be disposed over various portions of frames 76 depending on the direction of flow 32, the position of frames 76, and other factors known to those of ordinary skill in the art.

Figure 14A:
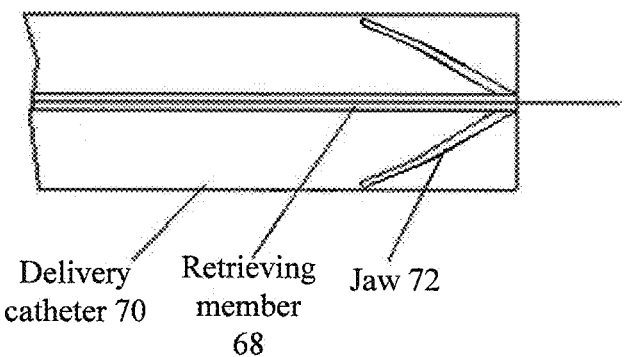
FIGS. 14A, 14B, and 14C illustrate an example of a retrieving member, in accordance with various embodiments of the subject technology.
Figure 14B:
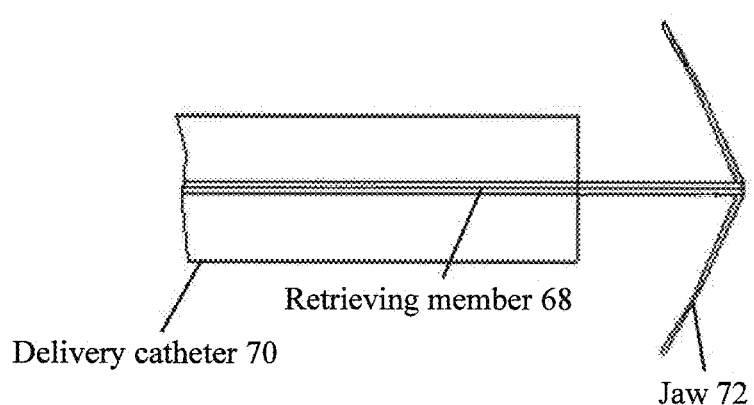
Figure 14C:
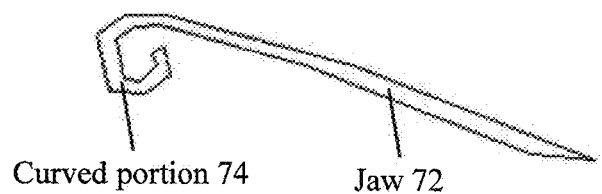

FIGS. 14A, 14B, and 14C illustrate an example of retrieving member 68, in accordance with various embodiments of the subject technology. Retrieving member 68 may be used to remove frame 76 and/or flow reducing member 14 from within a lumen. In some embodiments, retrieving member 68 may be stowed within delivery catheter 70, as shown in FIG. 14A. Delivery catheter 70 may be advanced to a position proximal to a site in which frame 76 and flow reducing member 14 are deployed. Retrieving member 68 may be deployed from within delivery catheter 70 and advanced distally toward frame 76. In some embodiments, retrieving member 68 may be advanced distally such that it may extend through flow reducing member 14. Retrieving member 68 is configured to couple to distal portion 24 of frame 76 and to retrieve distal portion 76 toward an interior of frame 76 for inverting frame 76. A separate retrieval catheter (not shown) may be positioned proximal to the site in which frame 76 and flow reducing member 14 are deployed for retrieving the inverted frame 76. In some aspects, delivery catheter 70 may extend through the retrieval catheter, and both of these catheters are positioned proximal to the site in which frame 76 and flow reducing member 14 are deployed.

In some embodiments, retrieving member 68 comprises at least one jaw 72 having a stowed position and a deployed position. The at least one jaw 72 is configured to expand from the stowed position to the deployed position, as shown in FIG. 14B, to allow the at least one jaw 72 to couple to distal portion 24. In some embodiments, the at least one jaw 72 may form an angle between about 45 degrees and about 60 degrees with respect to a central axis of retrieving member 68. In some embodiments, the at least one jaw 72 may comprise curved portion 74, as shown in FIG. 14C, so that curved portion 74 may hook distal portion 24 for inverting frame 76. In some embodiments, retrieving member 68 may comprise other means for retrieving frame 76. For example, retrieving member 68 may comprise alligator clips or other pinching means to grip a portion of frame 76 for retracting and/or inverting frame 76. In some embodiments, retrieving member 68 may couple to a proximal tip of elongate member 12, and retrieving member 68 may be used to retract frame 76 by applying a force to the proximal tip in the proximal direction to radially compress frame 76, allowing for its removal through the retrieval catheter or delivery catheter.

According to certain embodiments, occlusion provided by flow reducing member 14 may be permanent or temporary. In some embodiments, if temporary occlusion is desired, retrieving member 68 may be used to create an opening through flow reducing member 14 to restore flow therethrough. In some embodiments, frame 76 may be allowed to remain in the lumen after the opening through flow reducing member 14 has been created. This may be advantageous when occlusion is not desired anymore, but the removal of frame 76 is not a concern. In some embodiments, flow reducing member 14 may also be removed using the foregoing techniques as described above.

Figure 15:
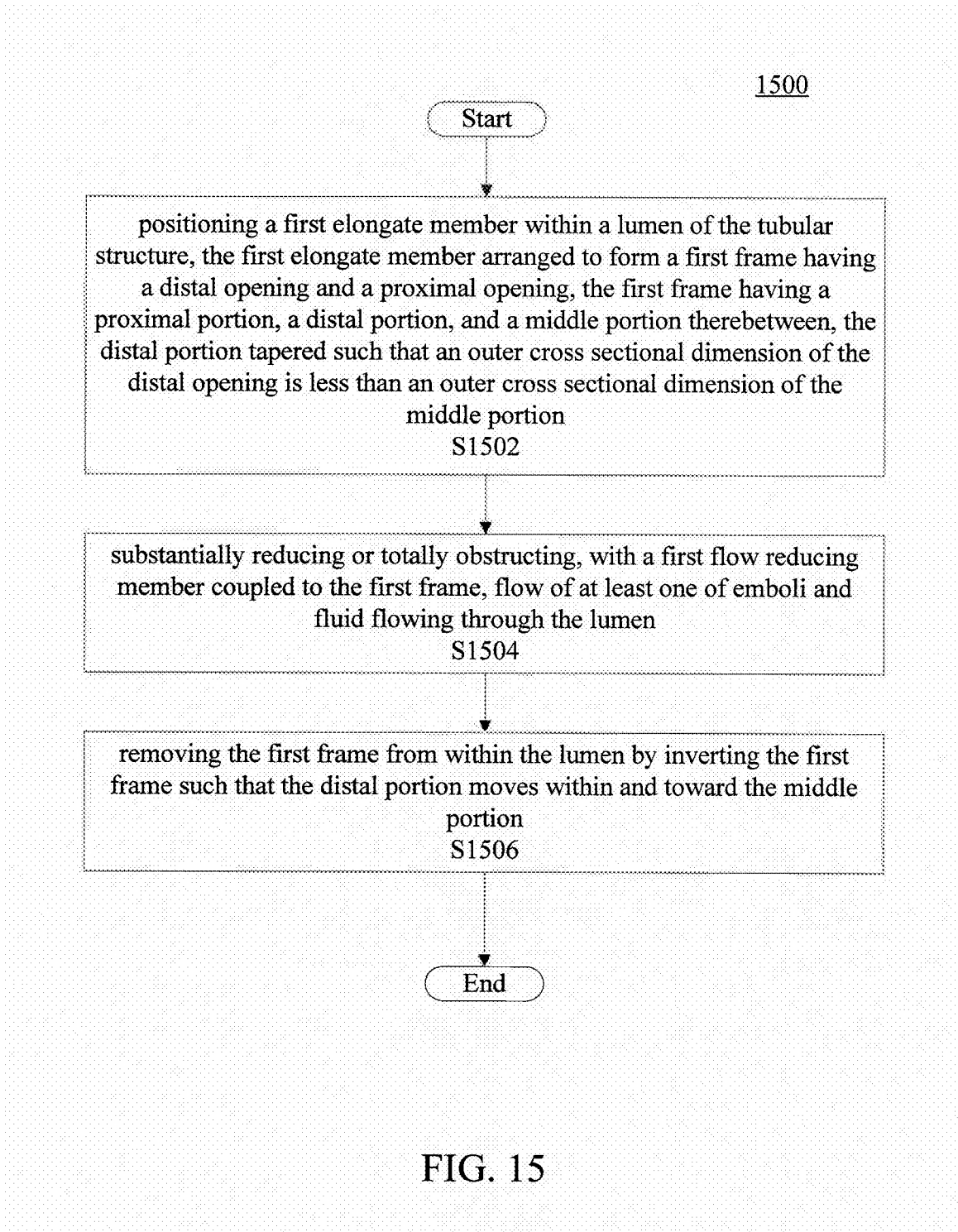
FIG. 15 illustrates an example of a method for reducing or stopping flow through a tubular structure of a patient, in accordance with various embodiments of the subject technology.

FIG. 15 illustrates an example of method 1500 for reducing or stopping flow through a tubular structure of a patient, in accordance with various embodiments of the subject technology. Method 1500 comprises positioning a first elongate member within a lumen of the tubular structure (S1502). The first elongate member is arranged to form a first frame having a distal opening and a proximal opening. The first frame includes a proximal portion, a distal portion, and a middle portion therebetween. The distal portion is tapered such that an outer cross sectional dimension of the distal opening is less than an outer cross sectional dimension of the middle portion. Method 1500 also comprises substantially reducing or totally obstructing, with a first flow reducing member coupled to the first frame, flow of at least one of emboli and fluid flowing through the lumen (S1504). Method 1500 also comprises removing the first frame from within the lumen by inverting the first frame such that the distal portion moves within and toward the middle portion (S1506).

Figure 16:
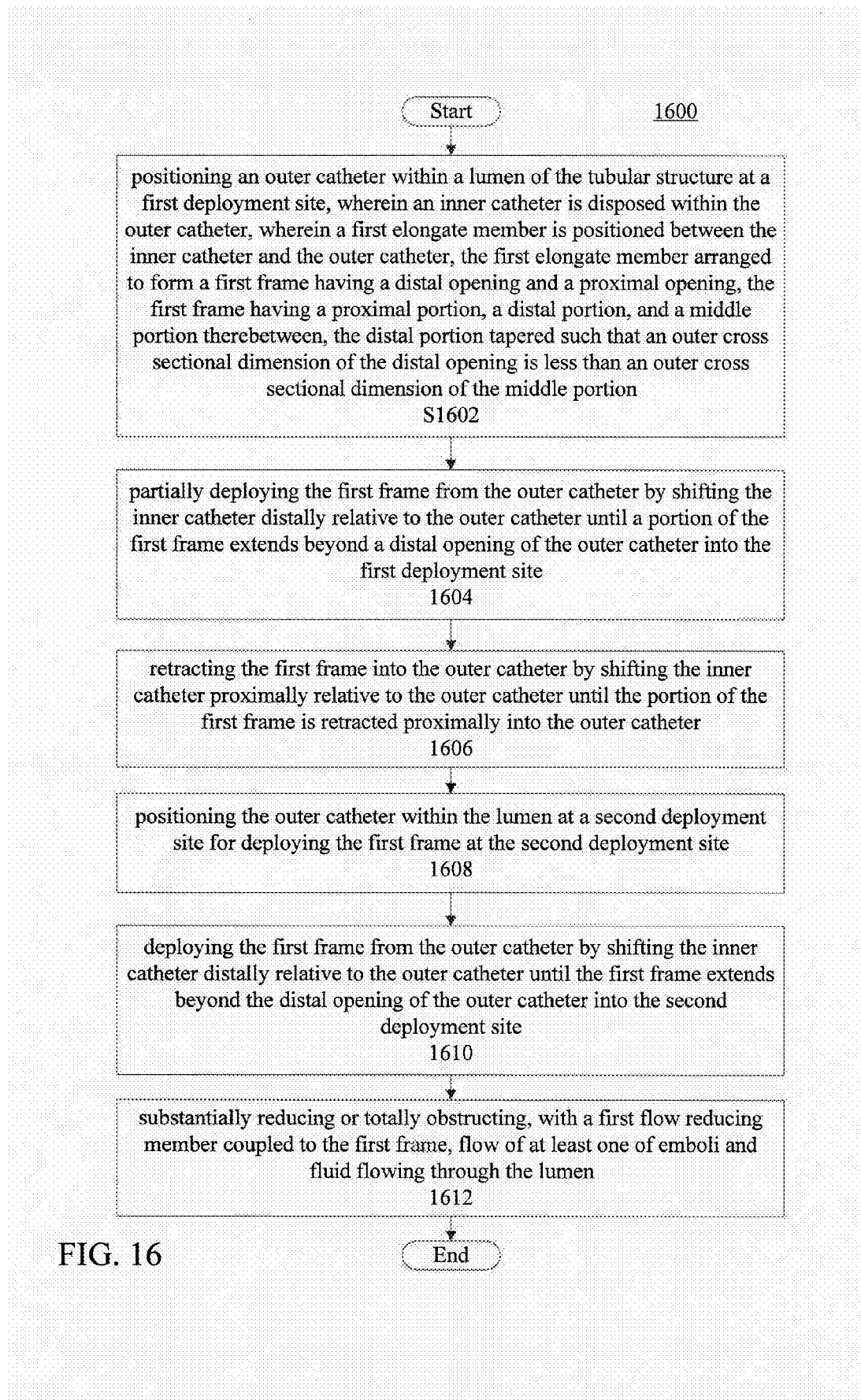
FIG. 16 illustrates an example of a method for reducing or stopping flow through a tubular structure of a patient, in accordance with various embodiments of the subject technology.

FIG. 16 illustrates an example of method 1600 for reducing or stopping flow through a tubular structure of a patient, in accordance with various embodiments of the subject technology. Method 1600 comprises positioning an outer catheter within a lumen of the tubular structure at a first deployment site (S1602). An inner catheter is disposed within the outer catheter. A first elongate member is positioned between the inner catheter and the outer catheter. The first elongate member is arranged to form a first frame having a distal opening and a proximal opening. The first frame includes a proximal portion, a distal portion, and a middle portion therebetween. The distal portion is tapered such that an outer cross sectional dimension of the distal opening is less than an outer cross sectional dimension of the middle portion.

Method 1600 also comprises partially deploying the first frame from the outer catheter by shifting the inner catheter distally relative to the outer catheter until a portion of the first frame extends beyond a distal opening of the outer catheter into the first deployment site (S1604). Method 1600 also comprises retracting the first frame into the outer catheter by shifting the inner catheter proximally relative to the outer catheter until the portion of the first frame is retracted proximally into the outer catheter (S1606). Method 1600 also comprises positioning the outer catheter within the lumen at a second deployment site for deploying the first frame at the second deployment site (S1608). Method 1600 also comprises deploying the first frame from the outer catheter by shifting the inner catheter distally relative to the outer catheter until the first frame extends beyond the distal opening of the outer catheter into the second deployment site (S1610). Method 1600 also comprises substantially reducing or totally obstructing, with a first flow reducing member coupled to the first frame, flow of at least one of emboli and fluid flowing through the lumen (S1612).

The foregoing description is provided to enable a person skilled in the art to practice the various configurations described herein. While the present invention has been particularly described with reference to the various figures and configurations, it should be understood that these are for illustration purposes only and should not be taken as limiting the scope of the invention.

There may be many other ways to implement the invention. Various functions and elements described herein may be partitioned differently from those shown without departing from the scope of the invention. Various modifications to these configurations will be readily apparent to those skilled in the art, and generic principles defined herein may be applied to other configurations. Thus, many changes and modifications may be made to the invention, by one having ordinary skill in the art, without departing from the scope of the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. An apparatus for reducing or stopping flow through a tubular structure of a patient, the apparatus comprising:
   a first elongate member arranged to form a first frame having a distal opening and a proximal opening, the first frame configured to be positioned within a lumen of the tubular structure, the first frame having a proximal portion, a distal portion, and a middle portion therebetween, the distal portion tapered such that an outer cross sectional dimension of the distal opening is less than an outer cross sectional dimension of the middle portion; and
   a first flow reducing member coupled to the first frame such that when the first frame is positioned within the lumen, the first flow reducing member substantially reduces or totally obstructs flow of fluid flowing through the lumen, the first flow reducing member being disposed over an exterior of the first frame and over the distal portion with at least a portion of the first flow reducing member extending from the exterior of the first frame into an interior of the first frame through the distal opening to form a single flap in the interior of the first frame, the single flap configured to operate as a one-way valve that moves in response to fluid flow to substantially prevent distal flow through the distal opening and to allow proximal flow through the distal opening.

2. The apparatus of claim 1, wherein the first elongate member is arranged in a spiral configuration to form the first frame.

3. The apparatus of claim 1, wherein the proximal portion is tapered such that an outer cross sectional dimension of the proximal opening is less than the outer cross sectional dimension of the middle portion.

4. The apparatus of claim 1, wherein the first elongate member comprises a substantially rectangular cross section.

5. The apparatus of claim 1, wherein the first flow reducing member comprises a plurality of pores each having a diameter of between about 5 microns and about 10 microns.

6. The apparatus of claim 1, wherein a thickness of a first coil of the first frame measured along an axial dimension of the first frame is less than a thickness of a second coil of the first frame measured along the axial dimension of the first frame.

7. The apparatus of claim 1, further comprising a retrieving member configured to couple to the distal portion and to retrieve the distal portion toward an interior of the first frame for inverting the first frame.

8. The apparatus of claim 1, further comprising:
   an outer catheter configured to be positioned within the lumen at a first deployment site; and
   an inner catheter disposed within the outer catheter,
   wherein the first frame is configured to be positioned between the inner catheter and the outer catheter for stowage of the first frame before the first frame is deployed within the lumen.

9. The apparatus of claim 8, further comprising one or more threads formed in or on an outer surface of the inner catheter such that the first elongate member wraps around the one or more threads for securing the first elongate member to the inner catheter.

10. The apparatus of claim 8, wherein the distal portion and the first flow reducing member extend distally beyond a distal opening of the outer catheter such that when the outer catheter is moved within the lumen to the first deployment site, the distally extended portion of the first flow reducing member is configured to engage a wall of the lumen to reduce friction.

11. The apparatus of claim 8, further comprising a guide wire extending through the inner catheter and the distal opening of the first frame.

12. The apparatus of claim 11, further comprising:
- a second elongate member arranged in a spiral configuration to form a second frame having a distal opening and a proximal opening, the second frame configured to be positioned within the lumen, the second frame having a proximal portion, a distal portion, and a middle portion therebetween, the distal portion of the second frame tapered such that an outer cross sectional dimension of the distal opening of the second frame is less than an outer cross sectional dimension of the middle portion of the second frame; and
- a second flow reducing member coupled to the second frame such that when the second frame is positioned within the lumen, the second flow reducing member substantially reduces or totally obstructs flow of at least one of emboli and fluid flowing through the lumen,
- wherein the second frame is configured to be positioned between the outer catheter and the guide wire for stowage of the second frame before the second frame is deployed within the lumen.

* * * * *